US 8,147,413 B2

(12) United States Patent
Abraham

(10) Patent No.: US 8,147,413 B2
(45) Date of Patent: Apr. 3, 2012

(54) IMAGE GUIDED CATHETER HAVING DEPLOYABLE BALLOONS AND PERICARDIAL ACCESS PROCEDURE

(75) Inventor: Theodore P. Abraham, Baltimore, MD (US)

(73) Assignee: InnoScion, LLC, Baltimore, MD (US)

( * ) Notice: Subject to any disclaimer, the term of this patent is extended or adjusted under 35 U.S.C. 154(b) by 34 days.

(21) Appl. No.: 11/871,219

(22) Filed: Oct. 12, 2007

(65) Prior Publication Data

US 2008/0183080 A1 Jul. 31, 2008

Related U.S. Application Data

(60) Provisional application No. 60/851,451, filed on Oct. 12, 2006, provisional application No. 60/953,861, filed on Aug. 3, 2007.

(51) Int. Cl.
*A61B 8/14* (2006.01)
(52) U.S. Cl. .................. 600/466; 600/407; 600/437
(58) Field of Classification Search .................. 600/427, 600/466, 467, 461, 462, 478
See application file for complete search history.

(56) References Cited

U.S. PATENT DOCUMENTS

| | | | |
|---|---|---|---|
| 3,556,079 A | | 1/1971 | Omizo |
| 3,625,793 A * | | 12/1971 | Sheridan et al. ............. 156/229 |
| 4,781,677 A * | | 11/1988 | Wilcox ............................ 604/28 |
| 4,869,258 A | | 9/1989 | Hetz |
| 5,106,368 A * | | 4/1992 | Uldall et al. .................... 604/43 |
| 5,152,277 A * | | 10/1992 | Honda et al. .................. 600/116 |
| 5,159,931 A | | 11/1992 | Pini |
| 5,181,514 A | | 1/1993 | Solomon et al. |
| 5,415,636 A * | | 5/1995 | Forman .................... 604/101.03 |
| 5,454,373 A | | 10/1995 | Koger et al. |
| 5,505,088 A * | | 4/1996 | Chandraratna et al. ......... 73/623 |
| 5,647,364 A * | | 7/1997 | Schneider et al. ............ 600/445 |
| 5,701,901 A | | 12/1997 | Lum et al. |
| 5,704,361 A | | 1/1998 | Seward et al. |
| 5,967,984 A | | 10/1999 | Chu et al. |
| 5,997,497 A | | 12/1999 | Nita et al. |

(Continued)

FOREIGN PATENT DOCUMENTS

CA 2 376 103 3/2001

OTHER PUBLICATIONS

International Search Report corresponding to International Application No. PCT/US2007/081185 dated Jul. 10, 2008.

(Continued)

*Primary Examiner* — Tse Chen
*Assistant Examiner* — Joel F Brutus
(74) *Attorney, Agent, or Firm* — Cameron LLP

(57) ABSTRACT

An interventional medical device that incorporates an imaging system may be minimally invasive and equipped with an anchoring portion that may be slidable and fixed in a predetermined position of its elongate body outside the human body, the device further comprising deployable first and second balloons for also securing the device to an internal wall, for example, within a human body. The medical device can be in the form of a catheter, a sheath or comprise interventional devices, particularly those suitable for minimally invasive procedures in the pericardium. The dual sealing/locking balloons may comprise a slidably moveable assembly for moving from a first position over an inflation channel to a second position over one inflation/deflation channel for separately inflating a distal balloon and then a proximal balloon to the patient's skin surface.

24 Claims, 24 Drawing Sheets

U.S. PATENT DOCUMENTS

| | | | |
|---|---|---|---|
| 6,149,598 | A | 11/2000 | Tanaka |
| 6,162,179 | A | 12/2000 | Moore |
| 6,306,097 | B1 | 10/2001 | Park et al. |
| 6,572,551 | B1 | 6/2003 | Smith et al. |
| 6,592,559 | B1 | 7/2003 | Pakter et al. |
| 6,689,062 | B1 | 2/2004 | Mesallum |
| 7,100,614 | B2 | 9/2006 | Stevens et al. |
| 7,270,634 | B2 | 9/2007 | Scampini et al. |
| 7,488,289 | B2 | 2/2009 | Suorsa et al. |
| 7,713,190 | B2 | 5/2010 | Brock et al. |
| 7,860,555 | B2 | 12/2010 | Saadat |
| 2001/0023323 | A1* | 9/2001 | Nishtala et al. .............. 600/567 |
| 2003/0229286 | A1* | 12/2003 | Lenker .......................... 600/462 |
| 2004/0015193 | A1* | 1/2004 | Lamson et al. ................... 607/9 |
| 2005/0001109 | A1* | 1/2005 | Walsh et al. .................. 248/74.3 |
| 2005/0090709 | A1 | 4/2005 | Okada et al. |
| 2005/0143664 | A1* | 6/2005 | Chen et al. ..................... 600/478 |
| 2006/0106315 | A1 | 5/2006 | Edens |
| 2006/0116627 | A1* | 6/2006 | Bridges et al. .................. 604/19 |
| 2007/0293724 | A1* | 12/2007 | Saadat et al. ................... 600/156 |

OTHER PUBLICATIONS

Non-final Office Action issued Oct. 13, 2011 in U.S. Appl. No. 12/285,779 related as continuation-in-part to the present application.

\* cited by examiner

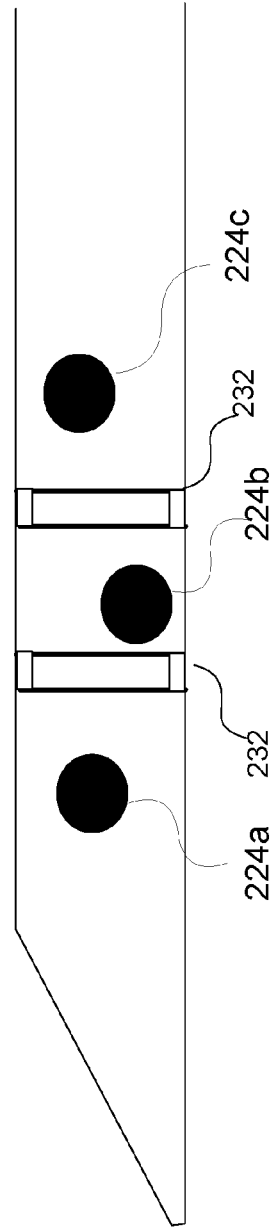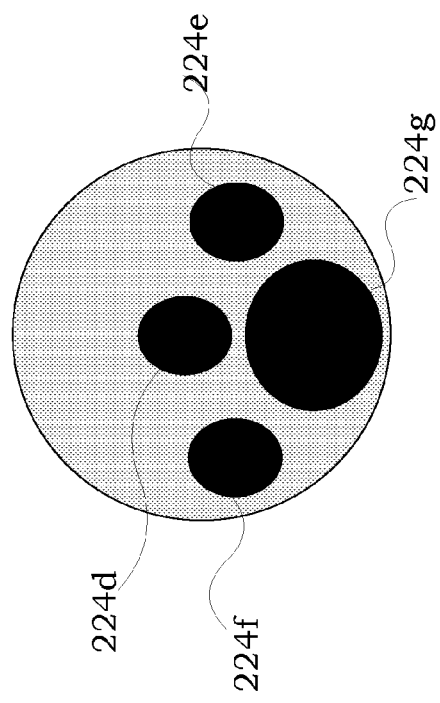
*FIG. 4A*
*FIG. 4B*

*Figure : Workflow scenarios (see text for details).*

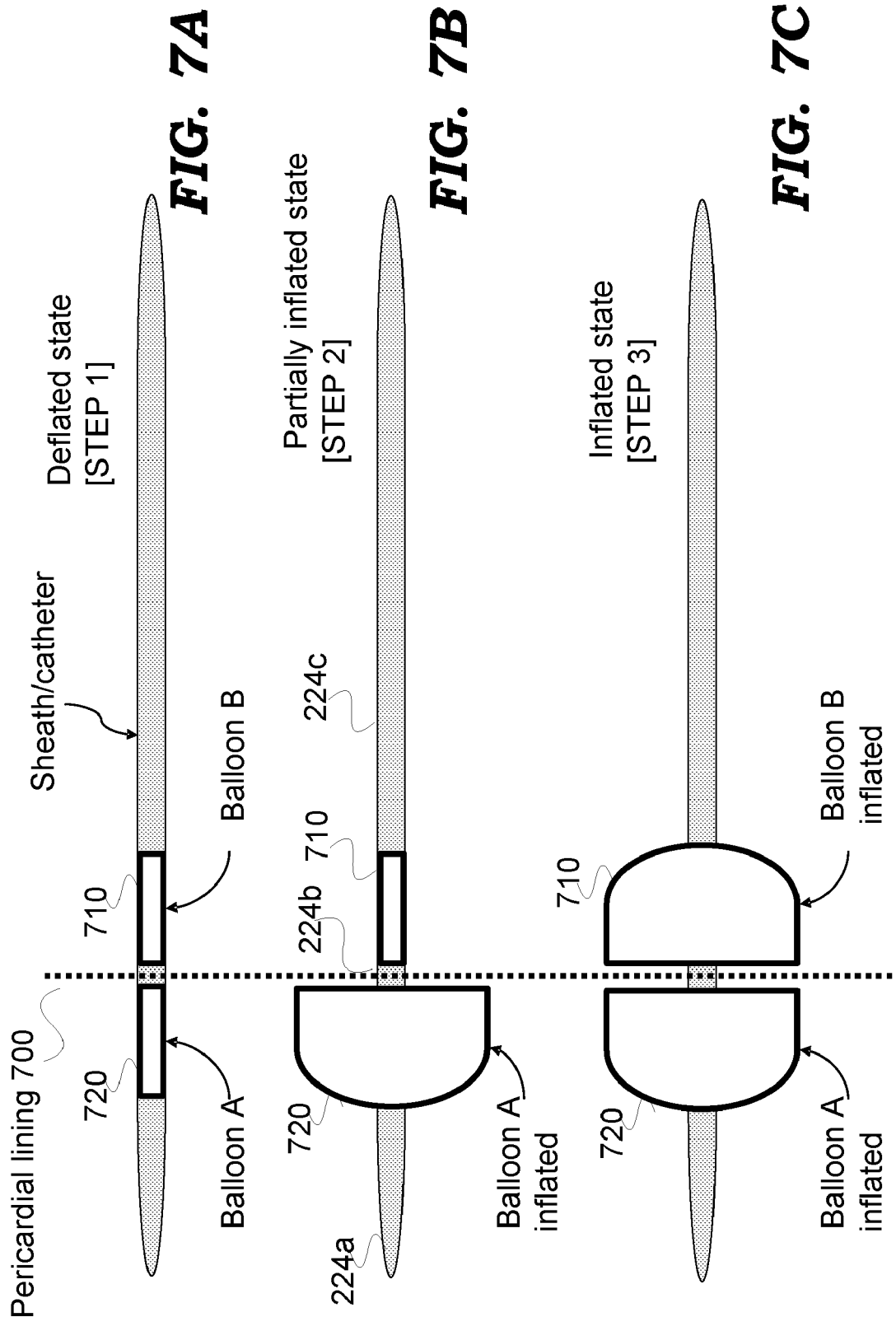

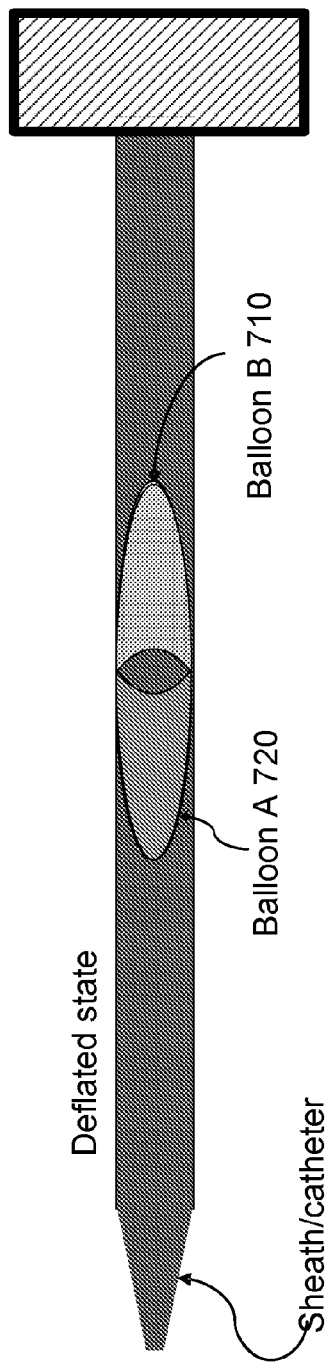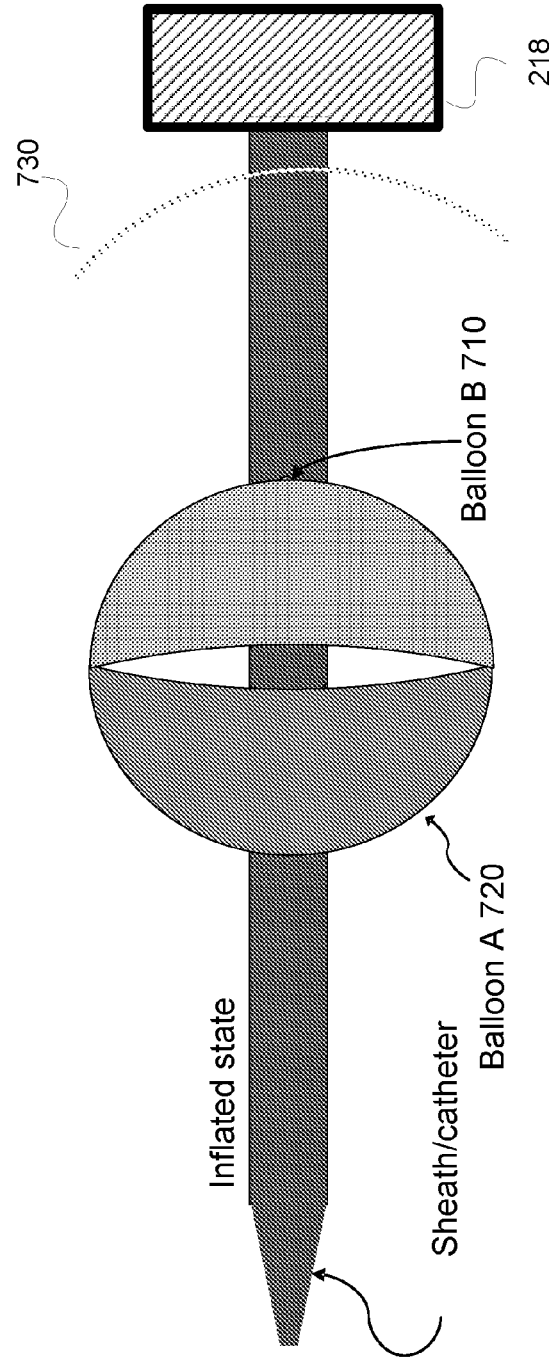

IMAGE GUIDED CATHETER HAVING DEPLOYABLE BALLOONS AND PERICARDIAL ACCESS PROCEDURE

CROSS-REFERENCE

This application claims priority to provisional U.S. Application Ser. No. 60/851,451 filed Oct. 12, 2006 and to provisional U.S. Application Ser. No. 60/953,861 filed Aug. 3, 2007, both of which are incorporated by reference herein in their entirety.

TECHNICAL FIELD

Embodiments of the illustrated and disclosed aspects and features relate to minimally invasive interventional medical devices having integrated imaging systems, a medical device, for example, having an integrated imaging system further including deployable balloons for securing the device to a wall pierced by the device, for example, the wall of a human organ and sealing such a wall, for example, a pericardial wall of the heart.

BACKGROUND

Ultrasound operates by creating an image from sound in three steps—producing a sound wave, receiving echoes, and interpreting those echoes to create an image. Invasive ultrasonic apparatus is known for imaging areas of the human body, for example, for guiding therapeutic instruments through a catheter to a field of view within a human body. For example, U.S. Pat. No. 5,704,361 to Seward et al. discloses a volumetric image ultrasound transducer underfluid catheter system.

FIGS. 2-9 and 11-12 and their attendant description, for example, suggest specific methods of intervention for imaging purposes in the vicinity of a human heart. To reach such an area of interest within a human body, an ultrasound imaging and hemodynamic catheter may be advanced via the superior vena cava to a tricuspid valve annulus. A distal end of a cylindrical body includes a guide wire access port, and a guide wire provides a means of assuring that the catheter reaches a target for imaging. A surgical tool may be fed through the catheter to the area imaged.

U.S. Pat. No. 6,572,551 to Smith et al. provides another example of an imaging catheter. Tools may be incorporated in an exemplary catheter, including suction, guide wire, or an ablation electrode.

U.S. Pat. No. 5,967,984 to Chu et al. describes an ultrasound imaging catheter with a cutting element which may be an electrode wire or a laser fiber. FIGS. 1 and 2 also describe a balloon 14 and a means to inflate the balloon. The balloon, for example, may be utilized to dilate a vessel having strictures imaged via the imaging catheter.

Other imaging catheters are known. For example, U.S. Pat. No. 6,162,179 to Moore teaches bending (using a pull wire) an acoustic window into a known and repeatable arc for improved three dimensional imaging. U.S. Pat. No. 6,306,097 to Park et al. discloses an ultrasound imaging catheter whereby a first lumen provides access for an ultrasound imaging catheter and a second lumen provides a working port for a tool. U.S. Pat. No. 5,505,088 to Chandraratna et al. teaches using a 200 MHz transducer in an ultrasonic microscope combined with a catheter as a delivery means for the microscope to provide imaging of myocardial tissue. According to Chandraratna et al., lower frequency ultrasound transducers can provide deeper penetration in the tissue but do not provide the image quality provided by higher frequencies.

In view of these references, it is suggested that ultrasound is a common imaging technique that can be used to visualize internal organs, and that various frequencies of ultrasound have various advantages and disadvantages, and that the applications that can be made of ultrasound can vary depending on the frequencies used. All the above-cited references are incorporated herein by reference in their entirety for understanding illustrated and discussed aspects and embodiments of devices and methods herein.

Ultrasound has many uses in medical applications. For example, ultrasound is routinely used during pregnancy to provide images of the fetus in the womb. Generally, a water-based gel is applied to the patient's skin, and a hand-held probe, called a transducer, is placed directly on and moved over the patient. The probe typically contains a piezoelectric element that vibrates when a current is applied. In ultrasound devices, a sound wave is typically produced by creating short, strong vibrational pulses using a piezoelectric transducer. The sound wave is reflected from tissues and structures and returns an echo, which vibrates the transducer elements and turns the vibration into electrical pulses. The electrical pulses are then sent to an ultrasound scanner where they are transformed into a digital image.

While general-purpose ultrasound machines may be used for most imaging purposes, certain procedures require specialized apparatus. For example, in a pelvic ultrasound, organs of the pelvic region can be imaged using either external or internal ultrasound. In contrast, echocardiography, which is used in cardiac procedures, can require specialized machines to take into account the dynamic nature of the heart.

Ultrasound has advantages over other imaging methods such as magnetic resonance imaging (MRI) and computed tomography (CT). For example, ultrasound is a relatively inexpensive compared to those techniques. Ultrasound also is capable of imaging muscle and soft tissue very well, can delineate interfaces between solid and fluid filled spaces, and shows the structure of organs. Ultrasound renders live images and can be used to view the operation of organs in real time. Ultrasound has no known long-term side effects and generally causes little to no discomfort to a patient. Further, ultrasound equipment is widely available, flexible, and portable. However, ultrasound does have some drawbacks. When used on obese patients, image quality is compromised as the overlying adipose tissue scatters the sound. The sound waves are required to travel greater depths, resulting in signal weakening on transmission and reflection back to the transducer. Even in non-obese patients, depth penetration is limited, thereby making it difficult to image structures located deep within the body. Further, ultrasound has trouble penetrating bone and, thus, for example, ultrasound imaging of the brain is limited. Ultrasound also does not perform well when there is gas present (as in the gastrointestinal tract and lungs). Still further, a highly skilled and experienced ultrasound operator is necessary to obtain and to interpret quality images, although software is known to assist in the interpretation process. These drawbacks do not, however, limit the usefulness of ultrasound as a medical diagnostic and treatment tool.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter.

Illustrative aspects described herein include a minimally invasive, interventional medical device that can provide ultrasound imaging coupled together with one or more interventional capabilities. The frequencies present in a sound wave output by such a device can range between 20 KHz and 300 MHz, wherein the lower frequencies, for example from 20 KHz to 1 MHz can be used, for example, to provide heat therapy to treat, for example, blood clots and the higher frequencies above 1 MHz can be used to provide high-resolution imaging, especially frequencies above 2o MHz.

An embodiment of a device in accordance with one or more aspects and features described herein can include an ultrasonic imaging catheter having one or more forward-directed transducers that can be integrated directly into a distal end of an elongate body so as to provide a direct forward view of the tissue being accessed. In one embodiment, a forward-directed transducer is mounted approximately 0.5 cm from a distal needle for imaging an internal organ wall to be pierced. At the same time, a camera may be used to image the area near the organ wall via an optic fiber and lens mounted near the needle. An alternative embodiment of a device in accordance with aspects described herein can have one or more ultrasonic transducers located along one or more sides of the elongate body, either with or without a forward-directed transducer. The ultrasound features of the device can serve to guide and facilitate surgical procedures performed with the device. For example, a medical professional such as a surgeon can receive direct vision of a targeted area in real time via a camera. The transducers mounted along the sides of the elongate body may be utilized to further image the vicinity immediately proximate the sides of the device such as a volumetric area for the deployment of locking and sealing balloons as will be further described herein.

In this embodiment or a related embodiment, the sides of one substantially cylindrical embodiment comprise first and second inflatable balloons disposed proximate to one another within indentations in the sides of the embodiment and in the vicinity of the one or more ultrasonic transducers located along the sides of an elongate substantially cylindrical body. A channel from the frontal (patient skin surface) end of the device is provided to each balloon separately for introducing inflating fluid, for example, liquid into each balloon such as saline solution. The solution used for balloon inflation may contain ultrasound contrast media that can be used to clearly delineate the balloon position by ultrasound. Such contrasting agents for ultrasound contrast are biologically inert compared, for example, with CT or MRI contrast which is relatively toxic to such organs as the kidneys. An example of a contrast agent is Definity® which is available from Bristol-Myers Squibb Medical Imaging or Albunex® available from Molecular Biosystems, Inc.; (further examples are Optison (GE) and Sonazoid). Each inflation channel may be provided with luer locks or other valve-like apparatus for maintaining the inflated state of the balloons, for example, at the proximal end of the elongate body.

The image provided by the ultrasonic transducers may assist an ultrasonic imaging machine operator to recognize the piercing of, for example, a pericardial wall. An operator of the device then can inflate a distal balloon proximate one or more signaling ultrasonic transducers and/or imaging fiber optics. A surgeon may pull the inflated distal balloon toward the pierced opening of the wall and then, optionally with the assistance of further imaging transducers and/or imaging fiber optics mounted in the vicinity of a second proximate balloon, inflate the second proximate balloon via a second channel provided thereto. The first and second inflated balloons operating together appear as a sandwich to the pierced wall, sealing the wall against leakage and locking the device in place.

With the device locked in place and the wall sealed, a biopsy or surgical procedure may be performed as further described below. Once the biopsy or surgical procedure is completed, the process of deflating the balloons and removing the imaging catheter begins in opposite order. For example, the proximate, second balloon is deflated by withdrawing liquid mixtures of contrast agent and saline solution or other filling material from the balloon. Then, the distal, first balloon is deflated by withdrawing balloon filling material from the balloon. The proximate side-mounted ultrasound transducers and/or camera imaging fiber optics may be used to visually assure that the balloons have been totally deflated. Then, the imaging catheter may be removed from the pericardial wall. During the removal process, any puncture hole left by the imaging catheter may be imaged, sutured shut and thus sealed if necessary.

In a related embodiment, it may be appropriate to provide a sliding balloon assembly slidingly mounted for movement, for example, of approximately one centimeter, for example, to permit the elongate body to be moved more closely to an operating site. The sliding balloon assembly may be positioned such that each balloon has sealed contact with the two inflating fluid channels. A guide wire and lumen to the sliding balloon assembly may be used to push or pull the balloon assembly along the elongate body to a position of interest within its permitted slidable length. In an embodiment related to this embodiment, the sliding dual balloon assembly utilizes only one inflation/deflation channel being sealed via appropriate lubricant to the elongate body. The distal balloon is mounted over, for example, a single inflating/deflating channel in a first position, inflated, and then the surgeon pulls on the elongate body to move the assembly to a second position over the same channel opening for inflation of the other balloon and, at the same time, move the distal inflated balloon to the internal organ wall. The second position is such that the second proximal balloon is now over the channel 236 and can be inflated, locking the elongate body to the wall. In reverse, when a procedure is concluded, the proximal balloon is deflated and the surgeon may pull on the elongate body to move the dual balloon assembly over channel 236 so the distal balloon may be deflated.

In such embodiments of a device in accordance with one or more aspects and features described herein, an ultrasound imaging transducer, optionally equipped with camera imaging fiber optics can be combined with an interventional catheter having an introducer needle so that the catheter can be inserted, for example, directly into an organ such as the heart through the chest wall without having to make entry through another means such as entry through a blood vessel in a human leg.

In another such embodiment in accordance with one or more aspects herein, a medical device is provided that can comprise one or more ultrasound transducers coupled or associated with a syringe element for fluid withdrawal or delivery. A wide variety of other interventional elements can be incorporated into such a device via a plurality of lumen such as biopsy devices or surgical cutting (scalpel) devices.

In additional such embodiments according to aspects herein, an interventional ultrasound device may include an elongate body having a proximal end and a distal end; one or more lumen extending through the elongate body; and one or more ultrasound transducers embedded in the elongate body near the distal end and camera imaging fiber optics. According to other aspects, at the proximal end of such a device, an anchoring portion is provided for anchoring the device to a human body once the device is image-guided and thus inserted therein so that the distal end reaches a region of interest within the human body in as minimally invasive a procedure as possible. The anchoring portion may be adjustable and fixed according to the length of the device via detents provided therein.

As discussed for a sliding balloon assembly, the proximal anchoring portion may be adapted for slidable movement so that the penetration depth of the elongate imaging catheter device may be regulated, for example, within a range of zero to two centimeters. The slidable anchoring portion this may either assist in anchoring the balloon assembly in a fixed position by providing a second anchoring position or may be used by itself as an anchoring position without a double balloon locking/sealing assembly.

According to aspects herein, the elongate body of such a device may be formed from one or more of a variety of materials such as silicone, Teflon, polyurethane, PVC, and/or elastomeric hydrogel. According to some aspects, the elongate body may be cylindrical in shape and may include, for example, a catheter or vascular sheath. According to other aspects, the elongate body may be provided with an off-axis handle as taught, for example, in U.S. patent application Ser. No. 11/871,282 filed concurrently herewith by Dr. Theodore Abraham entitled "Image Guided Catheters and Methods of Use" incorporated by reference in its entirety. The sheath may comprise the double balloon assembly and ultrasonic imaging capability as well as anchoring devices.

In use, such as in a minimally invasive surgical procedure, an elongate body member of such a device may be advanced to a target site of a patient while using the one or more ultrasound transducers and/or camera imaging fiber optics to guide insertion of the device; and the one or more ultrasound transducers and/or camera can image the target site while the minimally invasive surgical procedure is performed with the device anchored at the device by the anchoring portion. Optionally, wireless remote transducers may be utilized, for example, proximate the location of insertion of the device to generally provide images of, for example, the heart area and guide the insertion of the device into the chest cavity and through the wall, such as a pericardial wall, of interest as taught in U.S. Provisional Patent Application Ser. No. 60/953,861 filed Aug. 3, 2007, incorporated herein by reference in its entirety.

According to other aspects, such a device can be utilized in a variety of biopsy or surgical procedures and provide accurate guidance and imaging of a targeted area. For example, biopsies of, therapeutic procedures and surgeries on various organs and tissue such as myocardial, brain, muscle, lung, liver, kidney, uterine, ovarian, esophageal, stomach, intestinal, tumors, or other patient organs or tissue may be accurately performed with such a device.

Other vascular structures also can be effectively accessed and treated as desired with such a device including e.g. arteries, veins, lymphatics, and other hollow structures having walls such as the gastrointestinal tract, genitourinary tract, and respiratory system.

Devices as discussed herein can be effectively utilized for intracardiac treatments via pericardial access, without entry through blood vessels. That is, embodiments of the device may be inserted via a small incision as close, for example, to a pericardial lining location as possible through the patient's chest.

Such devices can also be especially useful in diagnosing and treating loculated or compartmentalized effusions in the heart (pericardial), abdomen (ascites), chest, or abscesses in any organ or body cavity. The real-time imaging (ultrasound and/or camera) that can be provided by devices of the invention can allow safe and accurate access to multiple compartments and ensure safe and complete drainage. Moreover, the sandwich balloons can both prevent leakage of liquids such as blood from an active organ such as the heart, kidney or lungs into another cavity such as the chest or abdominal cavity which may not be desired and lock the imaging catheter in a particular desired position for the further surgical, therapeutic or biopsy procedures.

In an exemplary procedure of accessing the pericardium and performing effusion, such a device can be advanced to a patient's pericardium while using the one or more ultrasound transducers/cameras to guide insertion and advancement of the elongate body of the device. Such an exemplary procedure can include puncturing the pericardial lining as the device is advanced while imaging the pericardial lining using the one or more ultrasound transducers and camera fiber optics; further advancing the elongate body into the pericardium; inflating the distal and frontal balloons to lock the device in place; inserting a guide wire through the lumen of the elongate body; advancing a sheath over the guide wire; and draining pericardial fluid or applying other therapeutic measures. A slidable anchoring device may be slided and locked via a detent to the skin of the patient under minimally invasive surgery to further secure the device at the desired location.

A further exemplary procedure for accessing the pericardium and performing a procedure on a target site of the pericardium can include advancing a device to a patient's pericardium while using the one or more ultrasound transducers/fiber optic camera imaging to guide insertion and advancement of the device's elongate body; puncturing the pericardial lining while imaging the pericardial lining using the one or more ultrasound transducers and camera; advancing the elongate body into the pericardium to a predetermined position; inflating the distal and frontal balloons to lock the device in place; optionally injecting material into the pericardium through the elongate body to create a pericardial pocket; deflating the balloons; inserting a guide wire through the lumen; advancing a sheath over the guide wire; inflating balloons of the sheath; inserting interventional and/or diagnostic devices through the sheath; and performing a pericardial procedure using the interventional and/or diagnostic devices.

The above process and devices are merely exemplary of different embodiments that may be applied for different purposes. For example, in the last-described process, having deployable balloons on the imaging device's elongate body may not be required, just the proximal anchoring device for securing the device after the imaging transducer array and/or fiber optic camera imaging at the distal end has successfully reached the site of interest. The sheath for performing the pericardial procedures may be equipped with the deployable balloons and no deployable balloons required on the elongate catheter device.

These and other aspects will be discussed with reference to the drawings, a brief description of which follows.

BRIEF DESCRIPTION OF THE DRAWINGS

The above-described aspects and embodiments of devices and procedures and other features and advantages can be appreciated and understood by reference to the following detailed description when considered in connection with the accompanying drawings wherein:

FIGS. 4A and 4B show side-mounted transducers and associated lumen for imaging an area of interest; in particular, side holes 224a, 224b and 224c may be proximate balloons 230, 232.

FIG. 6A shows different approach angles to a pericardial lining potentially highlighting a utility in having slidable anchoring means such as double balloons and/or a surgeon-side anchoring device to be mounted close to the patient's skin; FIG. 6B is for describing, for example, a remote wireless ultrasound transducer site that may be manipulated as per FIG. 6D while FIG. 6C provides exemplary circuitry for such a remote wireless device which can be used in combination, for example, with the device of FIGS. 1-5 as shown, for example, in FIG. 6E; FIG. 6F provides workflow scenarios for imaging and surgery; FIG. 6G provides a first view of a process for guiding a catheter and needle having double sealing/locking balloons to a pericardial lining at an access point; FIG. 6H shows a puncturing of the pericardial lining but the balloons have not yet reached the pericardial lining; FIG. 6I shows the device reaching a location of interest but the balloons have not yet been inflated; FIG. 6J shows the device with inflated balloons and a J type guide wire extended within a region of the pericardium of interest; FIG. 6K shows the first imaging device withdrawn and the insertion of a sheath and inflating its balloons at the pericardial lining over the guide wire; FIG. 6L shows the sheath inserted, balloons inflated and the sheath may now be used for deployment of surgical or biopsy instruments for special purposes.

FIGS. 7A-C the steps of inflating first and second balloons 710 and 720 to seal a pericardial lining and lock a sheath or catheter in place and the optional use of side-mounted transducers 224a, 224b and 224c at pericardial lining 700.

DETAILED DESCRIPTION

An Image-Guided Catheter

Figure 1A:
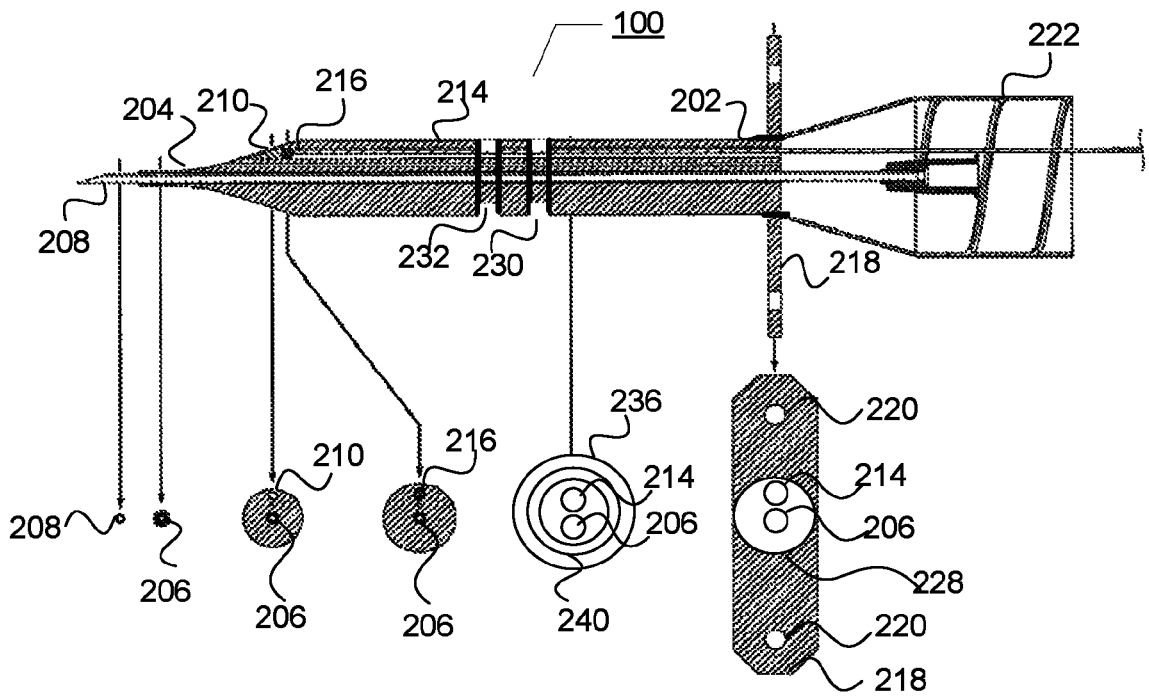
FIG. 1 shows a side cross-sectional view of one embodiment of a minimally invasive device in accordance with aspects described herein wherein FIG. 1A includes six cross-sectional views along the length of the depicted embodiment.
FIG. 1B provides a cross-sectional view of the embodiment of FIG. 1A and FIG. 1C provides further detail of the distal end of the device of FIG. 1A.
referring to FIG. 1D, locations 230 and 232 may show locations for proximate and distal balloons according to an embodiment for introduction of the device through a wall and channels 236, 240 used to inflate the balloons.
Figure 1B:
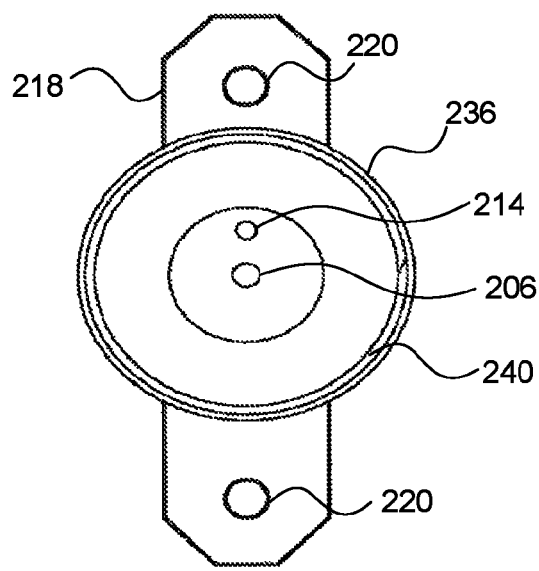
Figure 1C:
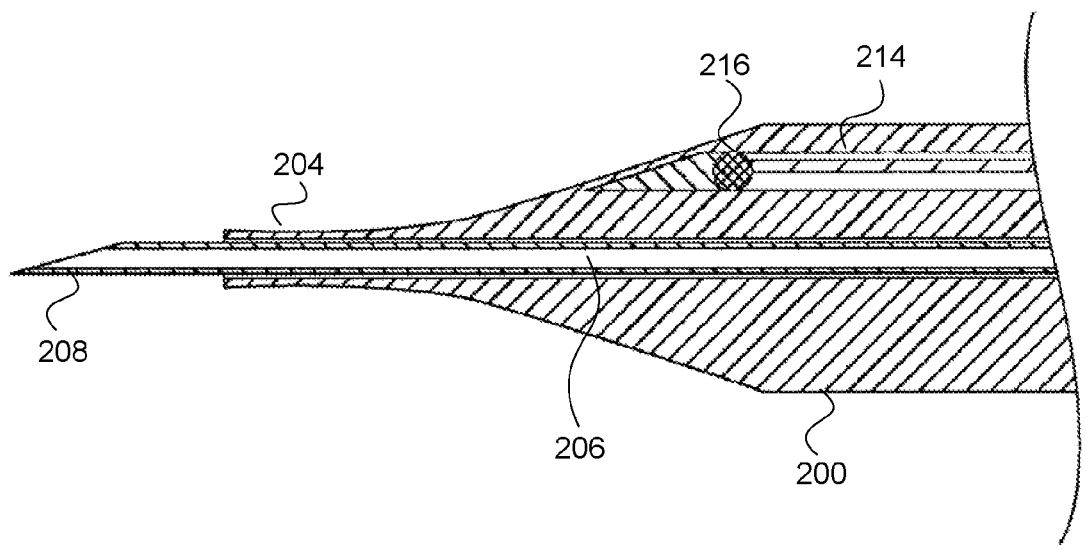
Figure 1D:
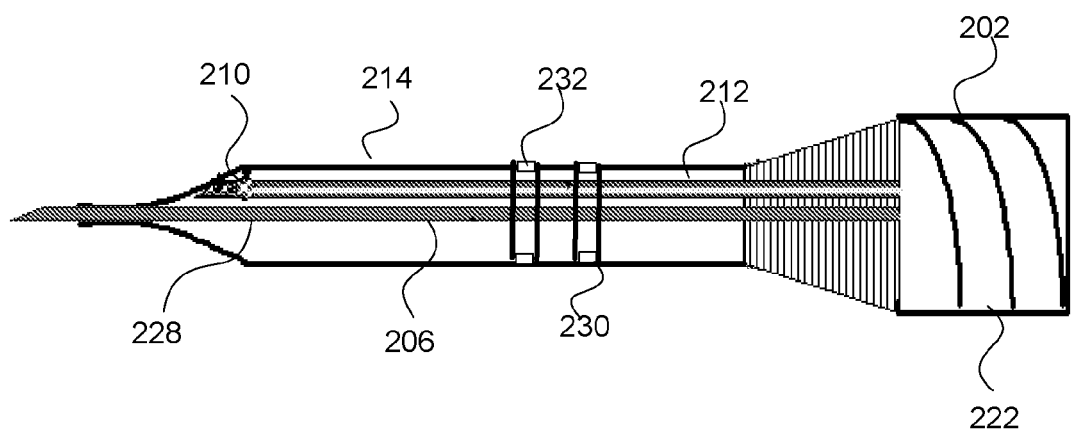

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made, without departing from the scope of the present disclosure.

The devices and methods of an embodiment of a minimally invasive image guided catheter and sheath and associated attachments and features primarily illustrated in FIGS. 1-5 and described herein can be used in minimally invasive surgical and other medical procedures. Following a discussion of embodiments of such medical device apparatus is a discussion of access procedures and methods utilizing the device embodiments in various ways as illustrated in FIGS. 6-8. Generally, a sheath for an imaging catheter device or an imaging catheter device itself, when used to pierce an internal wall or lining, for example, of an organ such as a heart, i.e. the pericardial lining, may be equipped with first and second inflatable balloons for sealing a piercing hole made in the organ wall or lining and locking the device or sheath in place for further procedures. While the embodiments described herein for using locking/sealing balloons are described with reference to internal uses, it is may be possible to utilize the double balloons at the skin surface for locking a catheter or sheath in external or outside the body applications, for example, in biopsy procedures when an organ has already been removed from a body. In addition, one skilled in the art will appreciate that the aspects and embodiments of FIGS. 1-5, although advantageously suited for such procedures on humans, can be used in veterinary procedures and in open medical techniques as well. Further, while the devices of the present invention are described with particular reference to catheters and sheaths for catheters, this shall not be construed as limiting the devices to these embodiments. It is contemplated and thus within the scope of the illustrated devices to adapt the devices and double balloon locking/sealing assembly described herein so as to be in the form of any type of minimally invasive device (e.g. syringes, sheaths, wires, forceps, biopsy instruments, clamps, retractors, etc.).

Further, while certain devices, systems and methods are described herein with particular reference to pericardial access devices, systems, and methods, this shall not be construed as limiting. It is contemplated to adapt the devices, assemblies, systems and methods described herein so as to be used in any of a number of procedures, including, but not limited to, various cardiovascular procedures, general microsurgery, biopsy, drug and device delivery, vascular procedures, urology, thoracic procedures, otorhinolaryngology (ear, nose and throat), orthopedic procedures, neurosurgery, gynecologic procedures, gastroenterologic and general procedures, colon and rectal procedures, pericardiocentesis, thoracentesis, ascites tap, ventricular lead placements, and electrical and electromechanical mapping of the heart to name some of many possible procedures wherein a double balloon lock/seal assembly may be employed with related imaging, for example, ultrasound or camera imaging. As such, it is contemplated that the specific design parameters, other characteristics set forth hereinafter, and methods in relation thereto shall be modified as required so as to provide the appropriate dimensions and geometries as required to perform such other techniques. For example, the length and diameter of the elongate device as herein described, is adapted to suit the particular conditions for a given procedure. Thus, the disclosure to follow should be construed as illustrative rather than in a limiting sense.

In general, the illustrated embodiments and aspects provide a device that couples an imaging system and a delivery system and/or minimally invasive interventional device to a double balloon assembly. The delivery system can include, for example, delivery of materials to or from a target site or delivery of instruments and devices to a target site. In certain embodiments, the device can comprise an ultrasound imaging catheter that incorporates one or more variable frequency ultrasound transducers operating at one or more frequencies within the frequency range of from 20 KHZ to 200 MHz. The imaging system (which may further include fiber optic camera imaging) guides and facilitates various procedures including the deployment of the double balloons, thereby significantly assisting in the access of and performance of procedures on various organs, structures and body cavities within the body, particularly during minimally invasive procedures. Ultrasound provides particular benefits because it is biologically safe and uses non-radiating energy to provide detailed anatomic and, in many cases, functional images. The images generated by the present devices provide a user with direct vision within the body in real time. Further, ultrasound provides a user with visualization of structures as well as within, beyond and through structures while camera imaging is limited to an immediate vicinity and to whatever the camera image may capture. The described devices and methods are compatible with many surgical and diagnostic devices and will allow bedside emergency procedures. In addition, the various frequencies of the ultrasound transducer can be used for different purposes and provide different beneficial results. For example, the lower frequencies such as those in the 20 KHz to 1 MHz range, produce heat as well as images, and can be used to provide therapy such as beneficial heat to the imaged tissues (for example, to break up blood clots). On the other hand, high frequencies, such as those in the 100 MHz to 200 MHz range can provide near microscopic resolution to the produced images and can be used for procedures requiring precision imaging of small structures or delicate tissues within centimeters of the ultrasound array.

The described devices and methods are suitable for use in a variety of medical procedures and, depending on the type of procedure, can be suitably designed and adapted for such use. In certain embodiments, the device can be in the form of any conventional catheters including, for example, biopsy catheters, ablation catheters, and mapping catheters. In certain embodiments, the present devices can be in the form of interventional devices (e.g. syringe, forceps, biopsy instruments, clamps, retractors, etc.) and/or are compatible with catheters, for example, biopsy catheters, ablation catheters, mapping catheters, and sheaths. In certain embodiments, the devices can be compatible with, for example, videoscopes and delivery needles such as those used for stem cell therapy. In still other embodiments, the devices can be compatible with fiber optics such as those used for vision therapy in combination with cameras or videoscopes.

Referring now to the various figures of the drawing wherein like reference characters refer to like parts, there is shown in FIGS. 1-5 various views of a minimally invasive device 100 and one or more embodiments. Devices for performing minimally invasive procedures, including sheaths (e.g., vascular sheaths), catheters, and interventional devices (e.g. forceps, biopsy instruments, clamps, retractors, etc.) are conventional in various forms as described above and, thus, although described and shown with reference to preferred embodiments, the general features (e.g. size, shape, materials) of the a device 100 may be in accordance with conventional devices or reduced in diameter as much as possible.

Figure 6A:
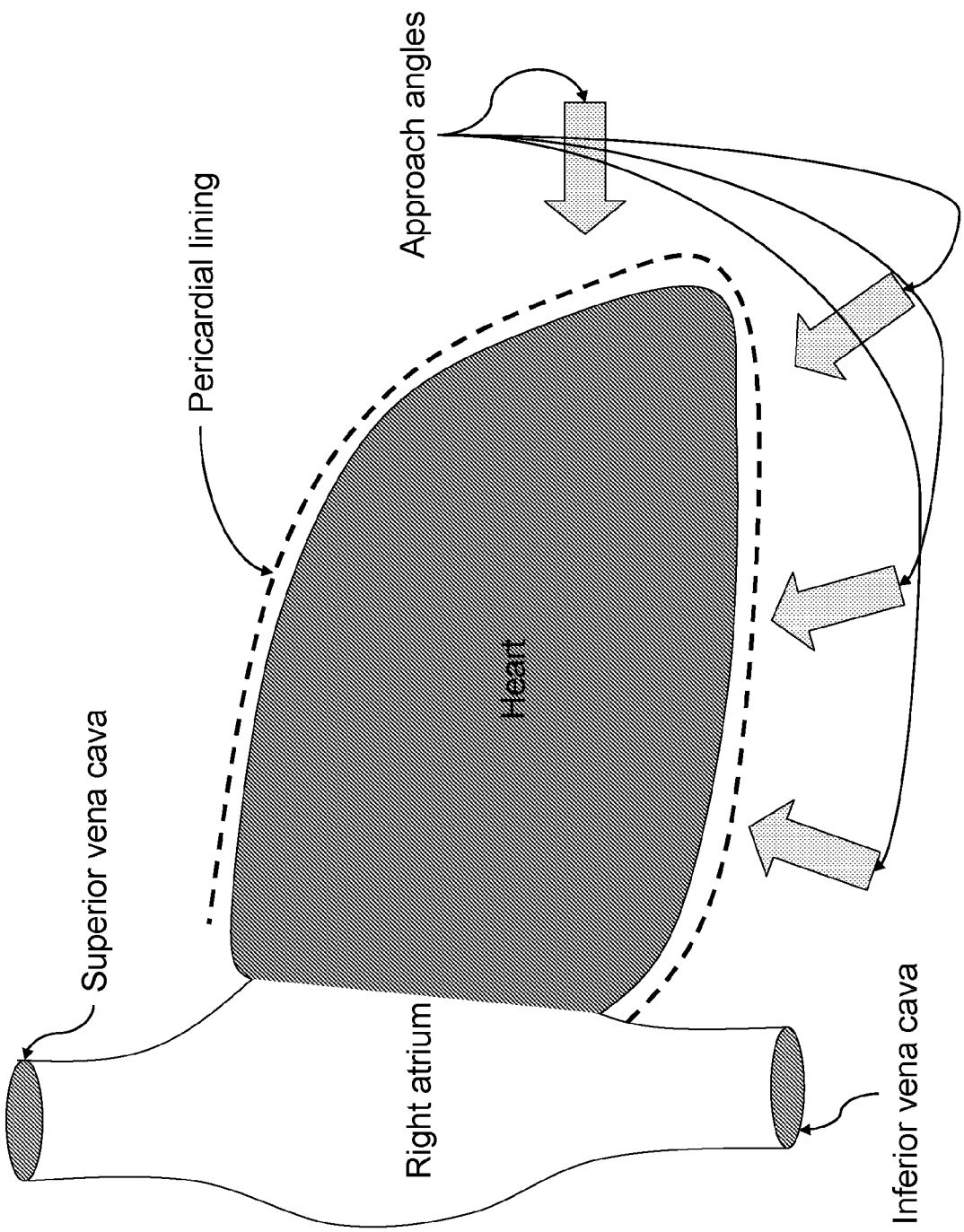
FIGS. 6A-L show side and cross-sectional views of embodiments of devices having different types of distal ends and various configurations of ultrasound transducers in accordance with one or more aspects.
Figures 1, 6B:
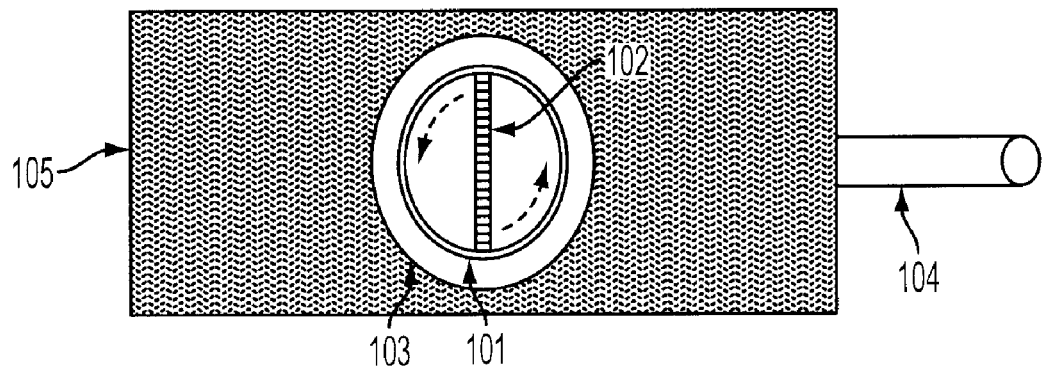
Figures 2, 6B:
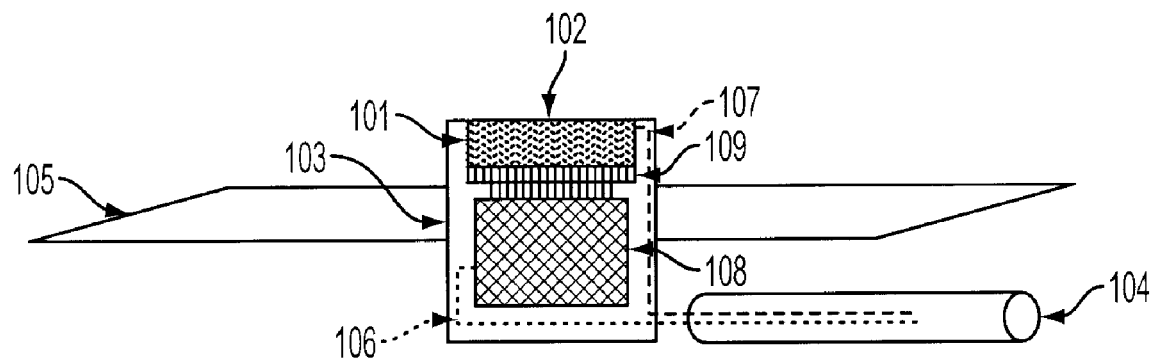

As shown in FIGS. 1 and 2, in one embodiment, the device 100 is in the form of a catheter and comprises an elongate body 200 having a proximal end 202 and a distal end 204. (In accordance with conventional practice, "proximal end" designates herein the specified end closest to the medical personnel manipulating the device, and "distal end" designates herein the opposite end placed within a patient).

The elongate body 200 can be fabricated of any conventional materials used in forming catheters, sheaths, and interventional devices. For example, when in the form of a catheter, the elongate body 200 can be fabricated of, for example, silicone, Teflon, polyurethane, PVC, and elastomeric hydrogel (AQUAVENE). In certain embodiments, the elongate body 200 is substantially cylindrical in shape.

The dimensions of the elongate body 200 are not particularly limited and can vary depending on the ultimate use of the device 100, the insertion point, and the distance to the target area from the insertion point. For example, the outer diameter of the elongate body 200 can be limited by the size of an anatomical structure that it is to be inserted in. The heart, for example, is generally within three centimeters of the body chest surface so a typical length from slidably moveable anchoring piece 218 to an area of operation, depending on the approach angle from FIG. 6A may be five to six centimeters for catheter/sheath device 100. The outer diameter of the elongate body 200 can also be limited based on the desired size of the incision through which the device 100 is inserted and which must subsequently be closed. For example, when the device 100 is in the form of a vascular sheath, the outer diameter can vary depending on the targeted blood vessel through which the elongate body 200 is inserted. Such devices, when in the form of vascular sheaths used during cardiac procedures, can be alternatively inserted through a blood vessel in the upper thigh or, alternatively, can be inserted through a blood vessel in the arm.

For example, in one embodiment, the device 100 can be inserted by anesthetizing an area the patient's upper thigh and inserting the elongate body 200 through a blood vessel in the upper thigh and towards the heart. In this embodiment, the elongate body 200 can have a length sufficient to traverse this pathway. The device 100 can also be in the form of a sheath used during a laparoscopic procedure, and in such a case, the elongate body 200 can generally have an outer diameter in accordance with conventional laparoscopic sheaths and will have a length that provides access to the target site. Further, the device can be used as a minimally invasive conduit from the skin surface to the target site to allow passages of catheters, guide wires, and instruments through elongate body 200. The elongate body 200 can be sized to allow these various instruments to be passed therethrough.

In an exemplary embodiment, and briefly referring to FIG. 7E, the device 100 can be in the form of a catheter that can be introduced directly through the chest cavity at location 730 to access various internal structures using minimally invasive techniques. As such, the elongate body 200 can have an outer diameter ranging from about 1 F to 15 F (wherein 1 F=0.33 mm) and a length ranging from about 1" to 20", preferably about six centimeters. Specific lengths and diameters can be provided based on the insertion site of the catheter, the distance to the desired target site(s), and the space required for insertion of one or more interventional devices through the elongate body 200.

In other embodiments, the device 100 can be in the form of any interventional device that can be, for example, inserted through a sheath or catheter to access various internal structures using minimally invasive techniques. As such, the elongate body 200 can have an outer diameter sized so as to fit within conventional sheaths or catheters, and a length suitable to access the desired target site(s) through the sheaths or catheters.

Figure 2A:
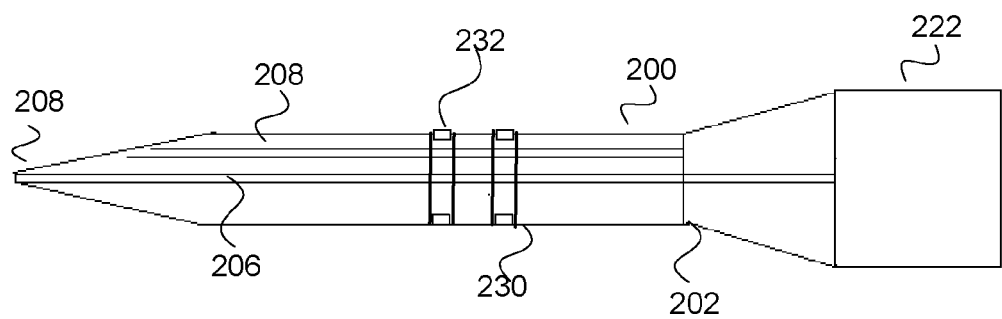
FIG. 2 shows a side cross-sectional view of the device of FIG. 1 without a needle housed within the device lumen and also showing locations for balloons 230 and 232 and channels to the balloons.
FIG. 2F shows details of one embodiment of a movably slideable balloon assembly for a sheath/catheter.
Figure 2B:
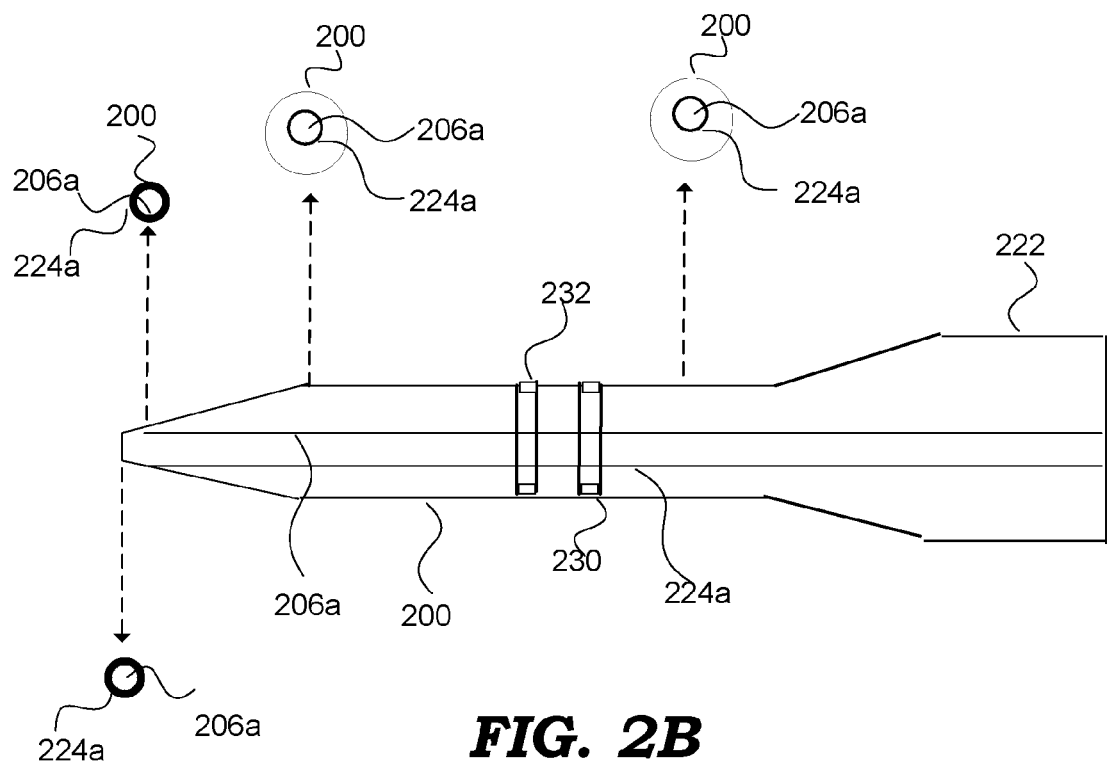
Figure 2C:
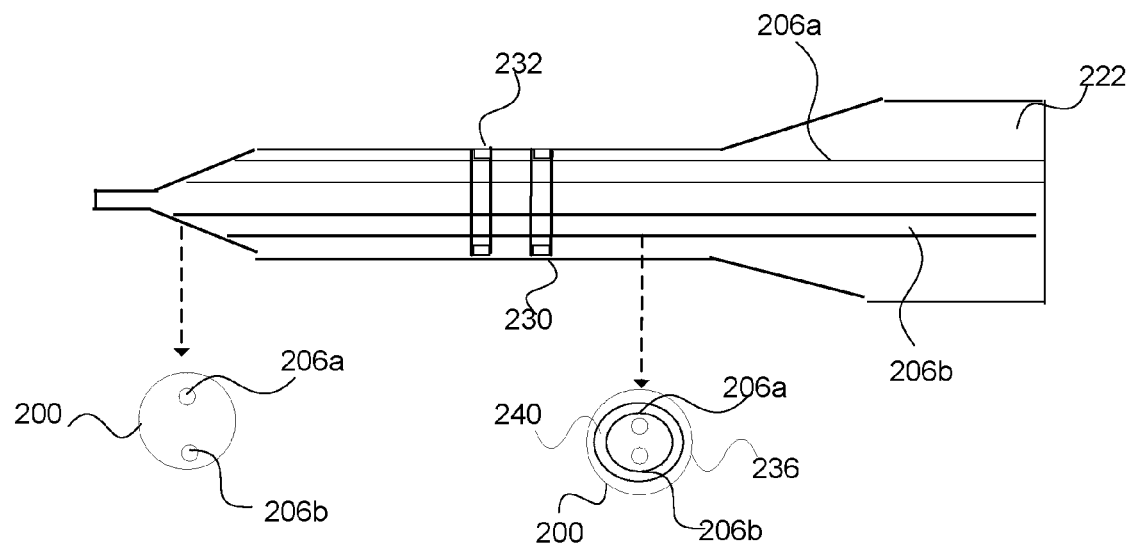
Figure 2D:
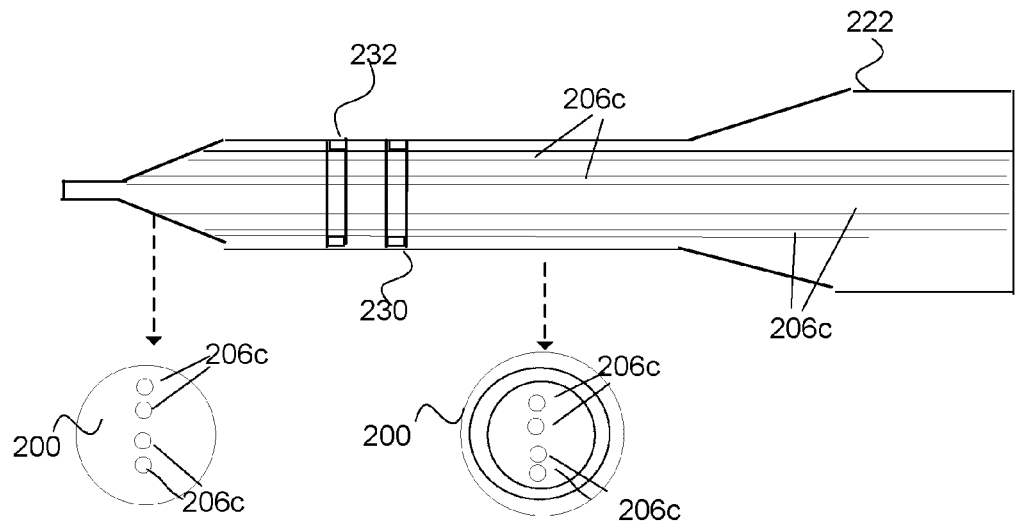
Figure 2E:
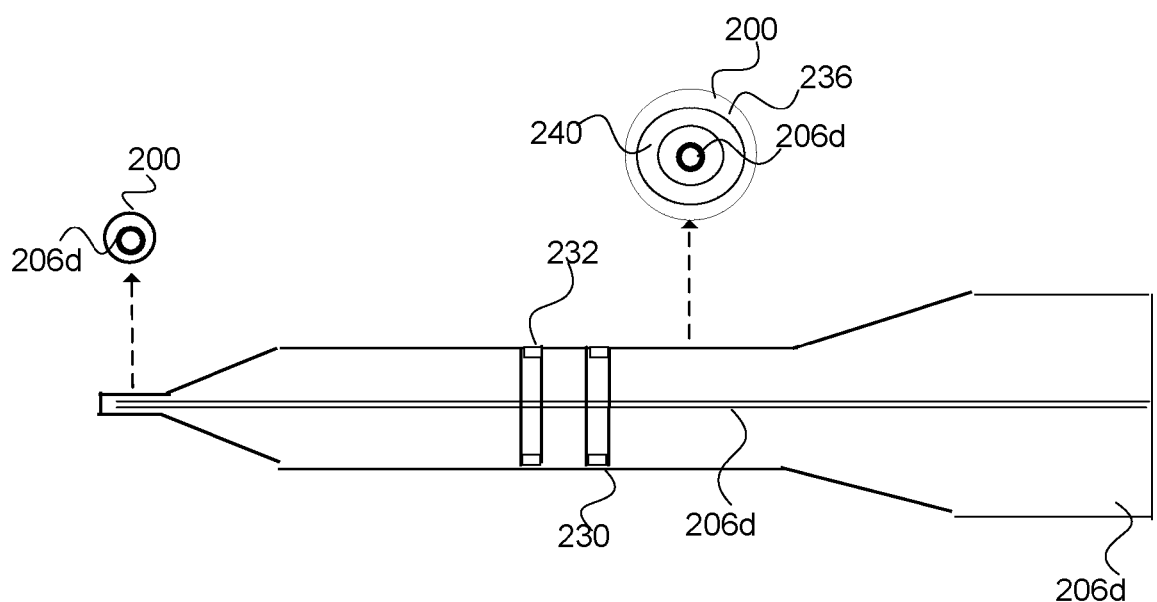

In certain embodiments, the device 100 can be in the form of a catheter or sheath and the elongate body 200 is provided with one or more lumen 206 extending therethrough. Depending on the use of the lumen 206, the design and configuration can vary. For example, in some embodiments as described further herein, a central wire lumen 206a can be provided through which a needle 208 is insertable (e.g., a lumen 206a running along the center of the elongate body 200 as shown in, for example, FIGS. 1, 2, and 7A). The needle can be used, for example, to puncture various target sites and inject or withdraw materials from a target site. As such, the lumen 206 can be, for example, at least 8-30 gauge so as to accommodate an 8-30 gauge needle 208. Of course, the central wire lumen 206a can be provided in other sizes to accommodate other sizes of needles 208. In some embodiments, the device 100 can be provided with one or more interventional device lumen 206b (for example, as shown in FIG. 2C) through which one or more interventional devices can be inserted and manipulated. As such, these lumen 206b can be sized so as to allow for insertion and manipulation of interventional devices therethrough. In some embodiments, the device 100 is provided with one or more injection/aspiration lumen 206c (for example, as shown in FIG. 2D) through which materials can be injected and removed. For example, emboli, blood clots and other materials can be evacuated from a blood vessel using an aspiration technique, and agents, such as medicaments, anticoagulants and contrast media may be injected into the treatment site using, for example, a syringe in connection with the lumen 206c. As such, these lumen 206c can be sized in accordance with conventional injection/aspiration lumen 206c. Camera imaging fiber optic lumen may terminate in a lens as close to the needle as possible to provide a camera view of an inner wall to be pierced such as a pericardial lining. In some embodiments, a guidewire lumen 206d (for example, as shown in FIG. 2E) can be provided through which a guidewire is inserted for steerable guidance of the device 100 into the desired site. As such, the lumen 206d can be sized to accommodate conventional guidewires. In some embodiments, the device 100 is provided with any combination of these lumen 206a, 206b, 206c, 206d. Further, in some embodiments the lumen 206a, 206b, 206c, 206d can be used interchangeably. For example, in one embodiment, three lumen 206 are provided and can be used to insert, for example, a fiber optic endoscope, a biopsy needle, and a therapy delivery needle. In some embodiments, up to five or more lumen 206 are provided, each having independent entry ports (not shown) for insertion and deployment of up to five or more independent medical devices and/or injection/aspiration through the device simultaneously or individually.

As shown in FIGS. 1, 2, 3A, 4A and 5 the elongate body member 200 can be tapered at the distal end 204. This shape is particularly suitable for use in, for example, accessing the heart through the chest through the pericardium. However, the distal end 204, 208 can be provided with other shapes such as, for example, rounded, square, beveled/angled, and pigtailed. In some embodiments, the tip is angled or beveled at any angle, for example, of 10°, at 20°, at 30°, at 40°, at 50°, at 60°, at 70°, or at 90°.

The distal end 204 of the body member 200 can be provided with one or more apertures 224 in connection with the one or more lumen 206. For example, one or more end apertures 224a (for example, FIG. 2B) can be located at the distal tip of the body member 200. In some embodiments, a central end aperture 224a is positioned at the center of the distal tip of the body member 200, as shown in FIG. 2B. In some embodiments, a plurality of side apertures 224a, 224b, 224c can be provided in the walls of the elongate body 200 (for example, as shown in FIG. 4A). A combination of one or more end apertures 224a and one or more side apertures 224a, 224b and 224c can be provided (for example, as shown in FIG. 4A where the side apertures are for imaging an organ wall between indentations for seal/lock balloons 230, 232). In one embodiment, up to 5-10 side apertures 224b, are provided depending on the application. The one or more of the apertures 224 can be provided with the same or varying diameters. The apertures 224, in connection with one or more lumen 206, can be used for injection and withdrawal of materials and insertion of various instruments (needles, guide wires, biopsy devices, etc.) In some embodiments, each aperture 224 is in connection with its own lumen 206. In other embodiments, one or more apertures 224 can share a one or more common lumen 206.

Figure 6C:
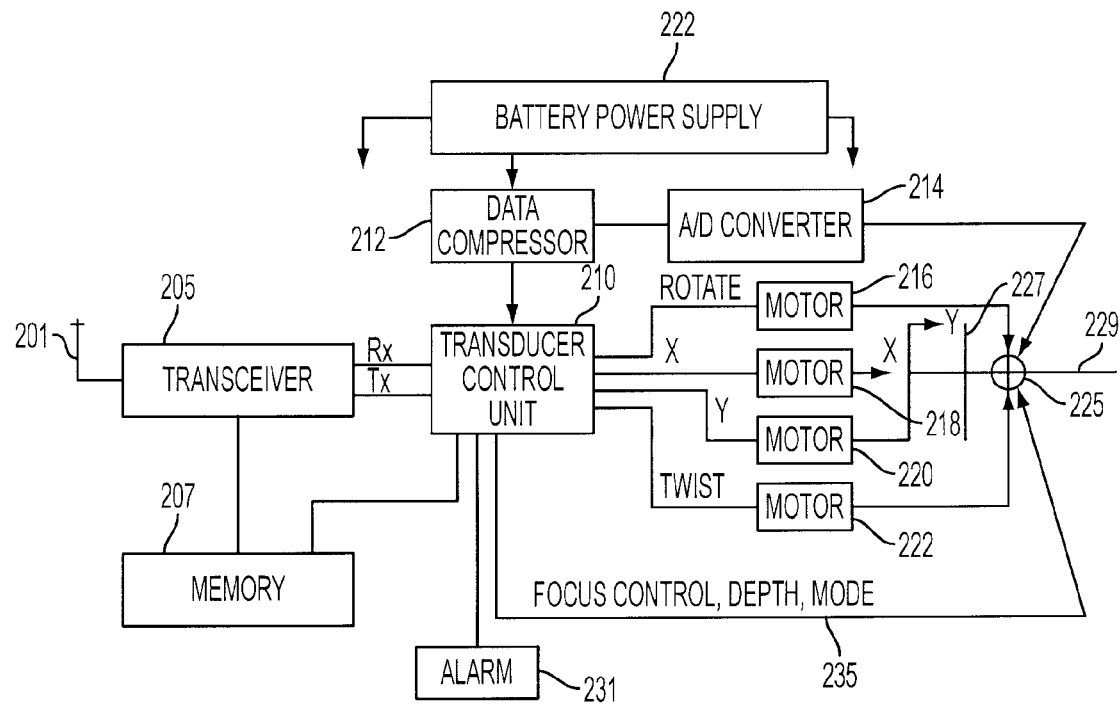

In some embodiments, one or more luer locks 222 are further provided at the proximal end 202 of the elongate body member 200. The luer lock 222 can be used to connect the device to, for example, a Touhey or a syringe (not shown) and one each may be used for one or two balloon inflation channels 236, 240 depending on the double balloon assembly construction described further herein. In some embodiments, a hemostatic valve and/or silicone pinch valve or water tight valve (not shown) can be located at the proximal end 202 of the elongate body 200 to prevent leakage of materials, such as blood and body fluids from the body and saline solution/contrast agent mixture if used to inflate the balloons, out of the device 100. In some embodiments, a side-arm (not shown) in fluid communication with one or more lumen 206 may also be located near the proximal end 202 of the elongate body 200. An aspiration device or syringe can be connected to the side arm, if desired, to aspirate blood clot and other materials through the lumen 206 or to inject water, saline, ultrasound contrast agent, a mixture thereof or similar material. These materials may be injected through the device 100 to a target site. Ultrasound contrast agent in saline solution may be used to inflate balloons 232, 234. Channels 236, 240 when filled with a contrast agent mixture will assist imaging from the surface by ultrasound imaging as discussed with reference to FIG. 6E showing remote surface transducers 710, 730 which may be manipulatable per FIG. 6D. More specifically, both the inflation and deflation of the balloons 232, 234 and the elongate body for the length of the body from the frontal end to the balloons may be viewed by, for example, ultrasound imaging from the skin surface via the use of contrast agent in the balloon inflating/deflating channel or channels.

The device 100 incorporates an imaging system, for example, ultrasound and/or camera that provides a user with visualization within the body during a procedure. The imaging system is particularly useful in minimally invasive procedures wherein direct visualization of the target site is unavailable. In one embodiment, the imaging system is in the form of an ultrasound system. Ultrasound systems are well-known and, thus, although described and shown with reference to a preferred embodiment, the general features and components of the ultrasound systems may be in accordance with conventional systems. The ultrasound imaging may be combined in one embodiment with imaging provided by a miniature video camera (not shown), preferably located as near to the distal tip as possible (while an ultrasound array captures a greater volume of body mass in its image).

As shown in FIG. 1, the imaging system includes one or more ultrasound transducers 210 that are positioned on the elongate body 200, for example, approximately 0.5 cm from the distal tip. In some embodiments, one or more transducers 210 are positioned very close to the distal end 204 of the elongate body 200 to provide imaging to a user as the device is guided to a treatment site. When the device is properly inserted and positioned at the target site, one or more transducers 210 provide images of the target site volume and one or more cameras may capture images of the site. In some embodiments, one or more transducers 210 can be provided on one or more sides of the elongate body 200 along its length. For example, as shown in FIGS. 4A-4B, any number of transducers 210 can be provided at any location along the elongate body member 200 in the vicinity of 224a, 224b and 224c for example. These same elements may comprise camera lenses/fiber optic lumen or both camera imaging and ultrasound volumetric imaging may be provided on the sides of member 200.

In general, a single transducer 210 may be operated at any given time to avoid crosstalk (harmonic interference) between different operating frequencies. In some embodiments, a plurality of transducers 210, having different specifications and frequencies of operation as desired, can be provided on a device at various locations to provide a user with various imaging/therapeutic capabilities. For example, front-facing transducers can be provided in combination with side-facing transducers to provide a user with the capability to view structures in front of the device as well as to the sides of the device, such as the pericardial lining when approaching the heart, operating at different frequencies. Further, different sized and types of transducers can provide a user with various imaging capabilities (e.g. different sized views, more or less precision, etc.).

Transducers 210 can be in accordance with conventional ultrasound transducers. For example, in some embodiments, the transducers 210 comprise piezoelectric materials such as PZT ceramics. The transducers 210 can also be of any size, with such size being limited by the size of the elongate body 200. As transducer size is decreased, the quality of the image provided may decrease. Thus, the smallest sized transducer that provides adequate imaging is generally used so as to minimize the required size required of the elongate body 200. For example 2-3 mm×2 mm transducers will generally require an elongate body of 5-6 Fr. In certain embodiments, the transducers 210 have a maximum dimension of 5 mm, in other embodiments 4 mm, in other embodiments 3 mm, and in other embodiments 2 mm depending on the application.

The transducers 210 can generally be mounted or attached to the elongate body 200 by providing one or more mounting aperture (not shown) in which the transducers 210 can be fit and held by a friction, adhesive or fasteners. Adhesives are known for holding transducers 210 in place.

Conducting elements 212 (for example, FIG. 1D), which can control one or more transducers 210, can extend from the transducers 210 to the proximal end 202 of the elongate body 200 and can connect to an external system (ultrasound scanner) such as a gray scale color two-dimensional Doppler ultrasound system. Conducting elements 212 can cause the transducer to emit the sound waves and transmit sound waves reflected from tissues and structures to an ultrasound scanner where they can be transformed into a digital image and the image displayed. The conducting elements 212 can extend through the elongate body member 200 within one or more imaging channels 214 (FIG. 1A, 1B, 1C, 1D). The imaging channels 214 can be provided in various sizes and, in exemplary embodiments, can range in size from 8-30 gauge.

To reduce ultrasound deflection during use of the device, the imaging system can be provided with matching layers 216 disposed adjacent, for example, to the front face of the transducers 210. The matching layers 216 can generally be in accordance with conventional matching layers and generally can include a matching layer front face and a matching layer rear face. The matching layers 216 can facilitate the matching of an impedance differential that may exist between the high impedance transducer elements and a low impedance patient. The matching layers 216 can generally be in accordance with conventional matching layers and can include a pocket with matching material that can reduce ultrasound deflection. Suitable matching layer materials can include, for example, plastic materials, such as polysulfone and REXOLITE® (a thermoset material produced by crosslinking polystyrene with divinyl benzene, available from C-LEC Plastics, Inc., Beverly, N.J.).

The imaging system may further include a backing layer (not shown) in accordance with conventional backing layers. The backing layers can generally be coupled to the rear face of the transducers 210 and function to attenuate acoustic energy that emerges from the rear face of the transducers 210. Generally, such backing layers can have a front face and a rear face, and can be fabricated of known acoustic damping material that possesses high acoustic loss.

In some embodiments, the device 100 can further be provided with one or more anchoring portions 218 at the proximal end 202 of the elongate body member 200. Due to different ultimate targets for surgical or other processes, the anchoring portion may be slidably moveable so that portion 218 may be moved along the length of an elongate body 200 and temporarily positioned there via a detent (not shown) or rubber washer and anchored to the human body surface to prevent further movement into or from the body than an ideal operating position. The anchoring portion 218 can assist in maintaining the device 100 in proper position during use and can prevent or inhibit unwanted motion of the device. If desired, one or more sutures (not shown) can be used with the anchoring portion 218 for suturing the device/anchoring portion 218 to the skin to provide additional stability of the device during use. For example, the anchoring portion 218 can be provided with one or more suture holes 220. The anchoring portion 218 may be slidably moved to a desired position and be temporarily fixed to a device 200 at a desired position by adhesive, mechanical or other known suitable fixer.

In applications where the device 100 is inserted and guided through a blood vessel towards a target site, one or more guidewires (not shown) may further be incorporated into the elongate body 200 for steerable guidance of the device 100, for example, into the pulmonary veins.

In some embodiments, the device 100 can be steerable and externally controlled. For example, the distal end 204 of the elongate body 200 can be manipulated by controls located on a portion of the device 100 positioned outside of the body during use. In some embodiments, one or more Micro-Electro-Mechanical Systems (MEMS) can be mounted on the device 100 at proximal and/or distal portions. MEMS systems include, for example, mechanical elements (beams, cantilevers, diaphragms, valves, plates, and switches), sensors, actuators, and electronics. MEMS also can be provided to function as tiny sensors and actuators. For example, MEMS can be incorporated in the device for measuring and monitoring pressure in the stomach or other organs in which the catheter is inserted, and for measuring and monitoring blood pressure when performing cardiac catheterization and be remotely controlled by the surgeon in known manner.

Referring to FIGS. 1-5, the device 100 can further incorporate one or more inflatable balloons 230, 232 at an intermediate position along the elongate body 200. In an exemplary embodiment, two balloons can be positioned approximately 2-10 cm from the distal tip of the catheter. In one embodiment, one or more ports 238, 242 (FIG. 3B) can be in connection with the balloons 232 via balloon inflation lumen or channels 236, 240 for infusion and removal of inflation/deflation material (e.g., saline and contrast agent). For example, ports 238, 242 can be provided with luer locks or other valve arrangements in a hub area positioned at the proximal end of the device 200 per FIG. 3B for inflation/deflation channels 236, 240. One or more valves (not shown) can be provided at the ports or within inflation lumen to prevent unintentional withdrawal or leakage of inflation/deflation material from the balloons 230, 232. In one embodiment, for example, as shown in FIGS. 4A-C, two balloons, a proximal balloon 230 and a distal balloon 232, are provided for locking/sealing an internal body wall. Each balloon is located in its deflated state in a corresponding indentation and secured at a frontal and distal end of the indentation all the way round the elongate body. Each balloon resembles an automobile tire in its inflated stated and collapses perfectly into indentations 230, 232. The inflation channels may feed inflation fluid or remove such fluid after use at any point within the indentation areas 230, 232.

Figure 2F:
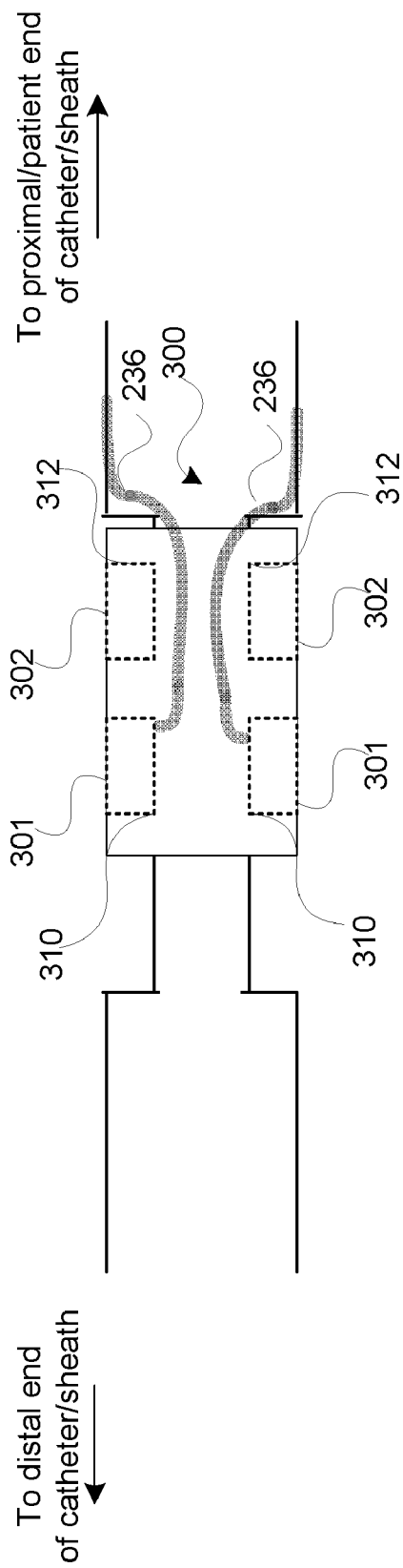
Figure 3A:
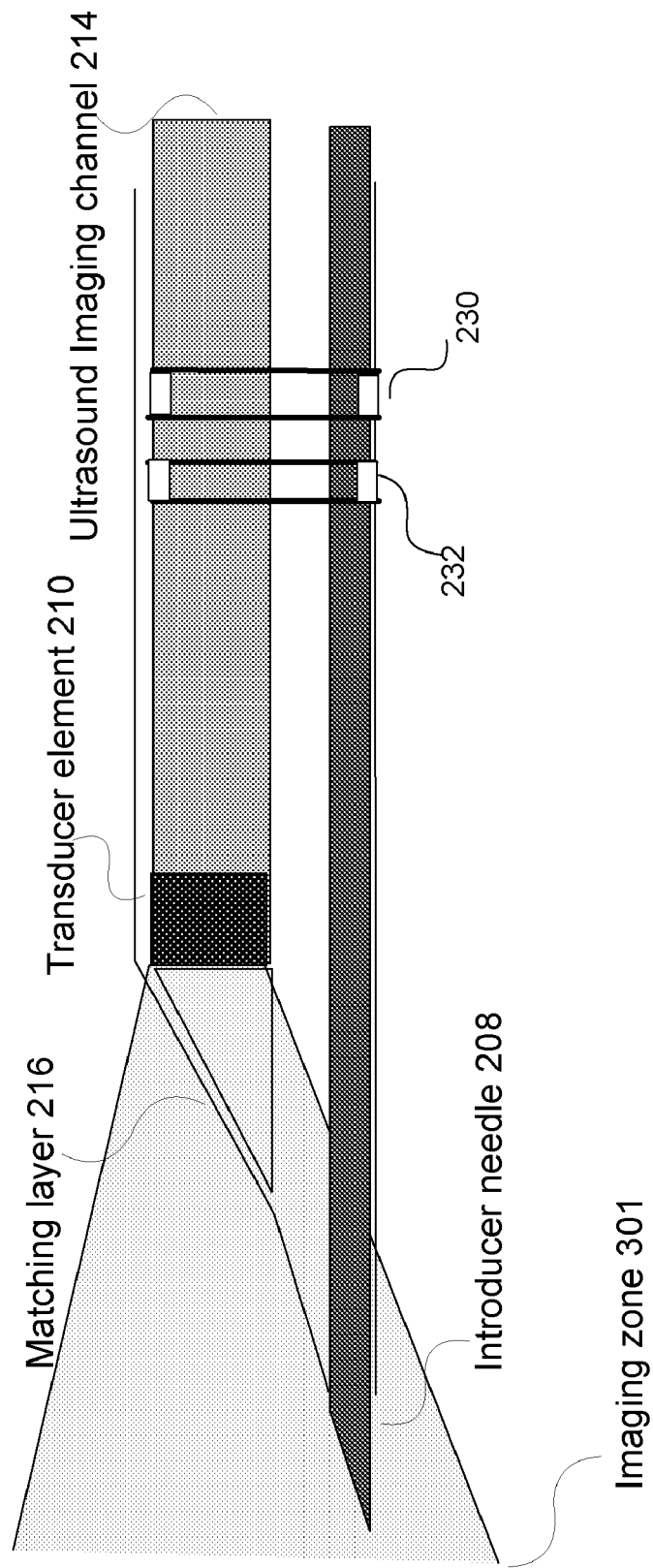
FIG. 3A shows the access instrument, patient end, including an imaging zone 301 and balloons 230 and 232 for sealing a wall and locking the device at a predetermined location.
Figure 3B:
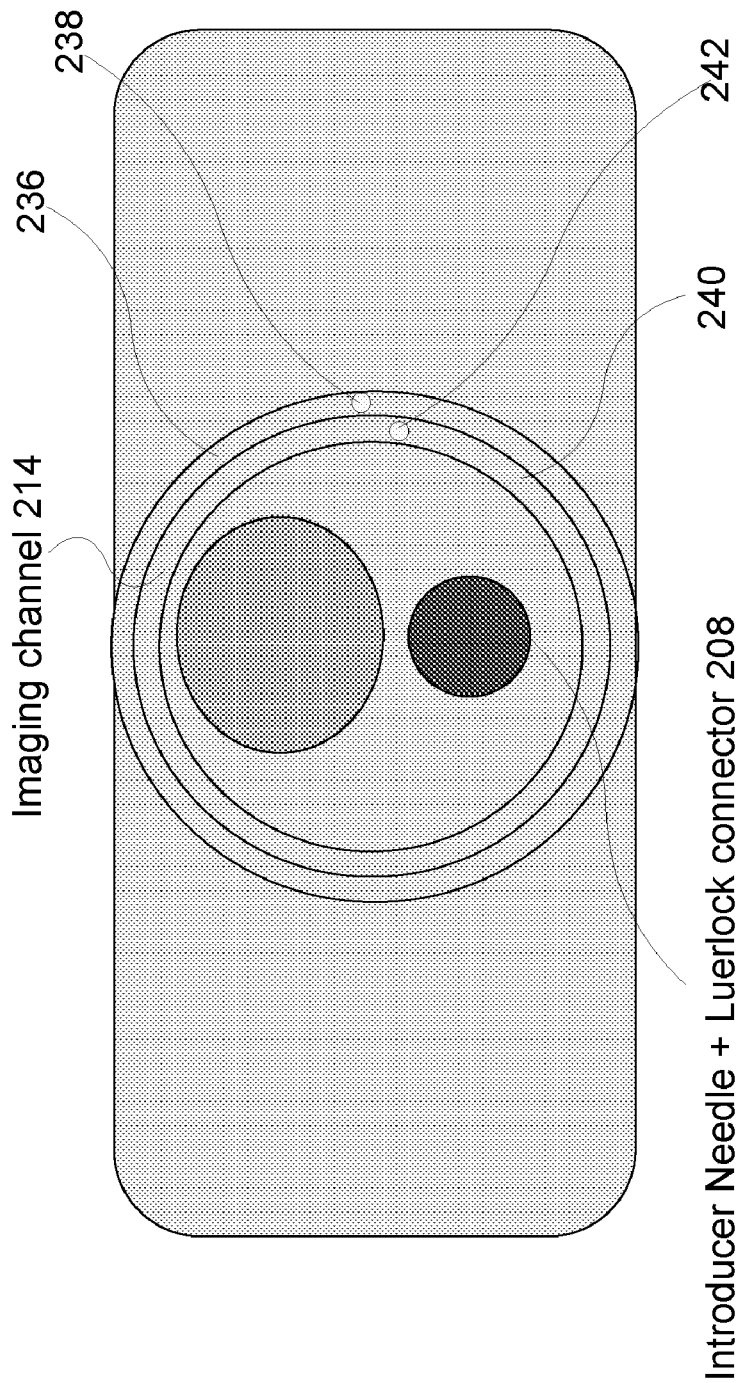
FIG. 3B shows the access instrument, operator end, including an imaging channel 214 and one of two inflating channels 236, 240 having corresponding inflating fluid entry points 238, 242 for luer locks.
Figure 5:
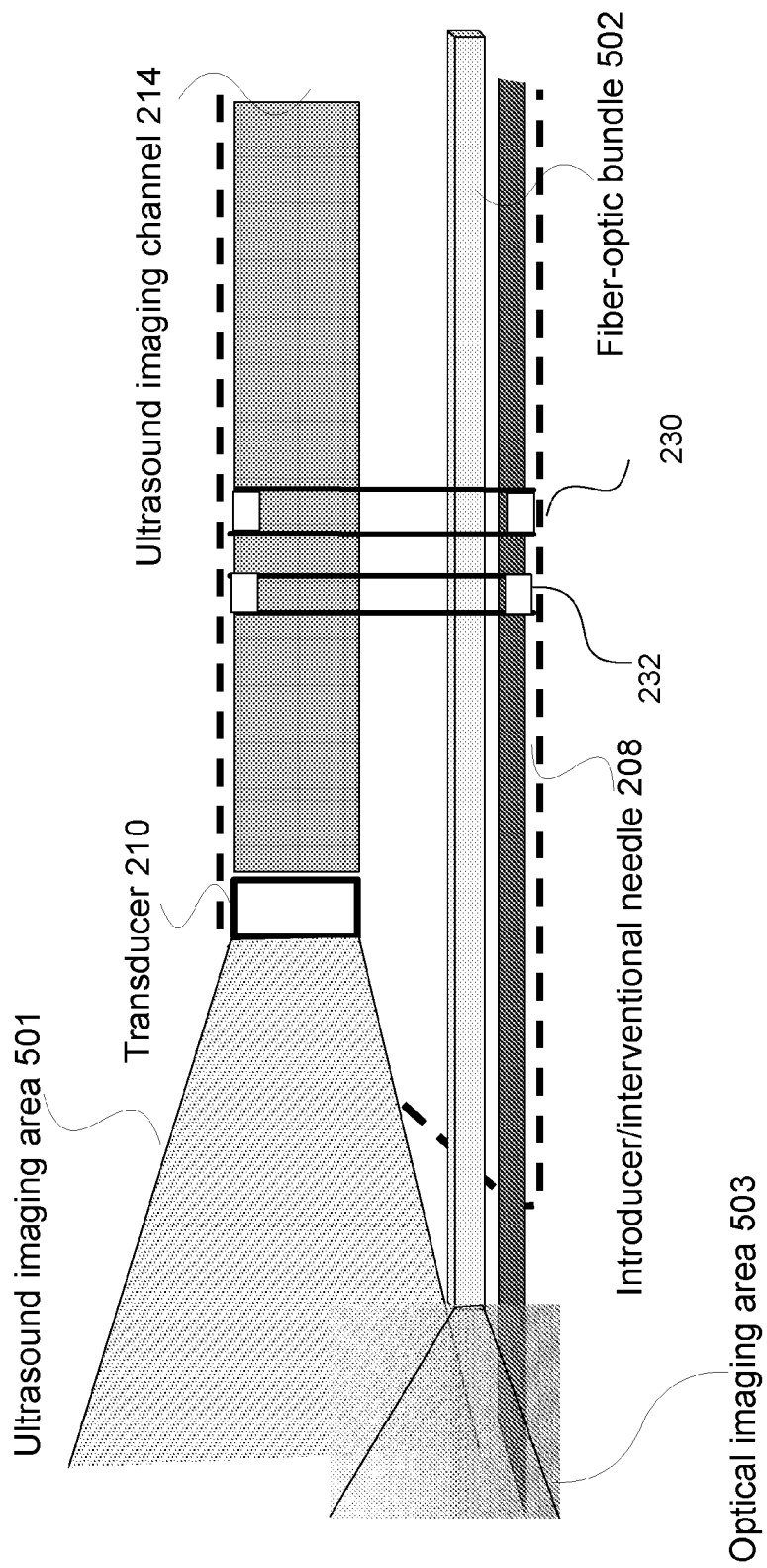
FIG. 5 shows a side view of another embodiment of a device in accordance with aspects herein including balloons 230, 232.

Referring briefly to FIG. 2F, in one embodiment, the two balloons are formed as a slidable assembly along the exterior surface of elongate body 200 and can be separately fed by permanently fixed inflation channels or a single channel within the region of slidability, for example, about one centimeter (single channel 236 shown).

Again referring to FIG. 2F, there is shown a slidably moveable assembly 300 having one inflation channel 236 shown. In a right-most position, the inflation channel is shown feeding a first indentation 310 (seen at top and bottom of a sheath/catheter) having balloon material 301 secured to ends thereof, the indentation an balloon material going all the way round the sheath/catheter (like a deflated tire). In a left-most position, the inflation channel 236 would be located proximate to the proximal indentation 312 having balloon material 302 secured to the frontal/distal ends thereof and extending all the way round catheter/sheath. Also, implicit in the embodiment of FIG. 2F is an embodiment in which dual channels 236, 240 may feed respective indentations 312, 310 respectively.

Referring briefly to FIGS. 7A-7C, when used for pericardial procedures, the elongate body 200 is advanced intrapericardially using the incorporated ultrasound system and/or a camera imaging system for guidance, for example, from the vicinity of the sternum at an approach angle to the pericardial lining. Once the distal balloon 232 is positioned intrapericardially per FIG. 7B, it is inflated as shown and the device 100 pulled back until the distal balloon 232 engages the inner surface of the pericardial wall lining 700. If the elongate body is now too far away from a target zone, a guide wire/lumen may be utilized to extend the elongate body toward the target zone again if, for example, the balloon assembly is slidably movable. If such is the case, the slidable anchoring portion 218 also may be slidably moved and used to doubly anchor the device 200 once the distal balloon 720 is in place. The proximal balloon 710 can then be inflated so as to engage the outer surface of the pericardial wall. In this manner, the pericardial wall 700 can be sandwiched between the proximal and distal balloons 232a, 232b to provide a relatively water-tight junction at the entry sight into the pericardium. Injection of fluids into the pericardium can be relatively leak-free as compared to injection without the use of the balloons. The use of ultrasound contrast agent in mixture with saline as an inflation/deflation fluid can improve the imaging of the balloons as well as assist the external imaging of the elongate device between the human body surface up to the region of the distal balloon 232, 720. The general features of the balloons 232, 230 or 720, 710 can be in accordance with conventional inflatable balloons. Any conventional materials used in forming balloons for medical and surgical procedures can be used such as, for example, silicone and Teflon. In general, the balloons should be able to withstand about 3 atm pressure. The balloons can be inflatable using any materials conventionally used to inflate such balloons including, for example, saline or mixtures of saline and contrast agent or the like. Gas may not presently be used, especially in the vicinity of blood vessels, due to the danger of a bursting gas balloon; for example, an air embolism may be fatal. Saline, on the other hand, even including an ultrasound contrast agent, is typically harmless in the event of a leakage from the balloon or balloon assembly.

In another embodiment in accordance with aspects herein, a luer lock syringe can be provided for connection with each of a plurality of luer locks 222. The luer lock syringe can be fastened to the device 100 to provide for saline injection or withdrawal, for example, withdrawal at the end of the procedure prior to removal of the device 100 from the treatment site.

In certain embodiments, the device 100 can be adapted for use in biopsy procedures including, but not limited to myocardial biopsy, brain biopsy, muscle biopsy, lung biopsy, liver biopsy, kidney biopsy, uterine and ovarian biopsy, esophageal biopsy, stomach biopsy, intestinal biopsy, tumor biopsy (anywhere), targeted biopsy of potentially abnormal zones in any of the above items (e.g., ultrasound guided biopsy of an abnormal area in the liver or kidney with the present catheter will allow access to the abnormal area, identification of abnormal zones by deploying the ultrasound and biopsy instrument to the specific area of interest). As such, the device 100 can, in some cases, be in the form of a catheter or sheath-like device that is insertable through small incisions in the body. The sheath-like device could include one or more lumen 214 through which a biopsy tool could be inserted. The device 100 in the form of a sheath could, thus, be provided along its length, as set forth above, with one or more ultrasound transducers 210 along with the other components required to provide ultrasound imaging using the transducers 210. In another embodiment, the device 100 could, itself, be a biopsy tool (either a minimally invasive biopsy tool that is insertable through a sheath or a biopsy tool that is directly insertable within the body). In this embodiment, the distal portion of the biopsy tool could include the mechanism for obtaining a biopsy (tissue sample) as well as one or more transducers 210, along with the other components required to provide ultrasound imaging using the transducers 210 as discussed herein.

In some embodiments, the device 100 can be used to provide access to vascular structures including arteries, veins, lymphatics, and to other hollow structures such as the gastrointestinal tract, genitourinary tract, and the respiratory system. As such, the device can be in the form of, for example, a vascular sheath. Such sheaths are well known, and, thus, the general features of the device 100 for these embodiments can be in accordance with conventional devices. The device 100 could further include one or more transducers 210, along with other components used to provide ultrasound imaging using the transducers 210 as discussed herein, camera fiber optic imaging as well as balloons or a balloon assembly for locking/sealing a wall or, for example, the gastrointestinal track.

In other embodiments, the device 100 can be used in procedures in various body spaces such as the pleural peritoneal space, pericardial space, perisphinal space, pelvis, and cerebrospinal space. For example, the device can be adapted for use in paracentesis, biopsy of any intra abdominal or intrapelvic organ, prostate biopsy, biopsy of tumors or otherwise suspected abnormal structures within the pelvis and abdomen, diagnosis of endometriosis, treatment by chemicals, cells, bio-agents, physical energy (e.g., cryo, radiofrequency, heat, laser) of any pathology within the pelvis and abdomen, visualization and application of therapy within the genitourinary tract, and drainage of abnormal or normal collection of fluid in actual or potential space in the abdomen, pelvis or genitourinary tract. The device 100 can be in the form of a catheter or sheath that provides entry into these various body spaces, thus allowing therapy delivery, intervention, placement of devices and diagnostics. The device 100 can also be in the form of interventional devices for use in procedures within these spaces. Such catheters, sheaths, and devices are well known, and, thus, the general features of the device 100 for these embodiments can be in accordance with conventional devices. The device 100 could further include one or more transducers 210, along with the other components required to provide ultrasound imaging using the transducers 210 as discussed herein. Procedures such as thoracentesis, ascites tap, biopsy of any organ, delivery of drugs or devices, can be made substantially safer and easier through the use of such devices by the imaging provided thereby. Other procedures that can be performed using the device 100 include procedures relating to diagnosis and treatment of infertility, including following a woman's ovum to determine an appropriate time for harvest, harvesting the ovum, and assisting in or performing the delivery of the fertilized egg to the uterus.

In some embodiments, the device 100 can be designed for use in cardiac procedures and for accessing various targets such as, for example, epicardial biopsy, electronic mapping (endocardial or epicardial), electromechanical mapping (endocardial or epicardial), endocardial or epicardial ablation using any form of energy, canulation or delivery of catheters, pacing leads, and interventional devices, mapping and access to the fossa ovalis and patent foramen ovale to enable crossing the atrial septum and allowing transvenous access to the left side of the heart, access to structures such as the coronary sinus and other cardiac venous structures, epicardial electrical and electromechanical mapping and ablation using any form of energy, pericardiocentesis, left ventricular lead placement, delivery of therapy (e.g., drugs, stem cells, laser therapy, ultrasound energy), epicardial coronary artery bypass, valve repair and placement, delivery of cardiac shape modifying devices (e.g., for ACORN®-like, MYOSPLINT®), myocardial scar reconstruction, ventricular reconstruction, ventricular assist device placement, and the treatment by chemicals, cells, bio-agents, physical energy (e.g., cryo, radiofrequency, heat, laser) of any pathology within the pericardial space or myocardium or intracardiac. As such, the device 100 can, in some cases, be in the form of a sheath-like device that is insertable through, for example, an incision in the patient's upper thigh and through a blood vessel all the way up to the heart. In such embodiments, guidewire can be provided within the device. Alternatively and often preferably, the device can be inserted through the pericardial space. The device 100, in the form of a sheath, could, thus, be provided along its length, as set forth above, with one or more ultrasound transducers 210 along with the other components required to provide ultrasound imaging using the transducers 210. In other embodiments, the device 100 can be in the form of a device that is used in performing the cardiac procedure (e.g. biopsy, or valve repair instruments) and can be provided with one or more transducers 210, along with the other components required to provide ultrasound imaging using the transducers 210 as discussed herein.

In other embodiments, the device 100 can be in the form of devices for use in performing procedures on the musculo-skeletal system and for accessing the musculoskeletal system, such as, for example, the treatment by chemicals, cells, bio-agents, physical energy (cryo, radiofrequency, heat, laser) of any pathology within the joint cavity, joint components, or muscle and bone, visualization and application of therapy involving muscle, bone, and joint components, including joint cavity, and drainage of abnormal or normal collection of fluid in actual or potential space in the muscle, bone, or joint components. In these embodiments, the device 100 can be in the form of a catheter or sheath that provides access to the musculo-skeletal system, thus allowing therapy delivery, intervention, placement of devices and diagnostics. The device 100 can also be in the form of interventional devices for use in procedures on the musculo-skeletal system. Such catheters, sheaths, and devices are well known, and, thus, the general features of the device 100 for these embodiments can be in accordance with conventional devices. The device 100 would further include one or more transducers 210, along with the other components required to provide ultrasound imaging using the transducers 210 as discussed herein.

In some embodiments, the device 100 can be in the form of devices for use in procedures on the brain and nervous system and for accessing the brain and nervous system. For example, such devices can be used for the treatment by chemicals, cells, bioagents, physical energy (cryo, radiofrequency, heat, laser) of any pathology within the cranium and spinal and penspinal space including the vasculature contained within, visualization and application of therapy within the cranium, spinal, and peri-spinal space and all contained vasculature, drainage of abnormal or normal collection of fluid in actual or potential space in the cranium, spinal, and pen-spinal space and all contained vasculature, and for transcatheter delivery of interventional devices such as aneurysm clips, hematologic treatments, and any other drug or non drug therapy, either directly or via the vasculature or via any other hollow structure within the cranium, spinal, and peri-spinal space and all contained vasculature. In these embodiments, the device 100 can be in the form of a catheter or sheath that provides access to the brain and system, thus allowing therapy delivery, intervention, placement of devices and diagnostics. The device 100 can also be in the form of interventional devices for use in procedures on the brain and nervous system. Such catheters, sheaths, and devices are conventional, and, thus, the general features of the device 100 for these embodiments can be in accordance with conventional devices. The device 100 would further include one or more transducers 210, along with the other components required to provide ultrasound imaging using the transducers 210 as discussed herein. Generally, the higher the ultrasonic frequency, the higher the resolution but the smaller the volume that may be imaged while lower frequencies are used for therapeutic purposes and provide low resolution but longer distance image capture.

In some embodiments, the device 100 can be in the form of devices suitable for use in procedures on the vasculature procedures and for providing access to the vasculature. For example, the devices can be adapted for visualization and application of therapy within the body vasculature and for the delivery of devices or drugs including stents, and any form of energy to the vasculature. In these embodiments, the device 100 can be in the form of a catheter or sheath that provides access to the body vasculature, thus allowing therapy delivery, intervention, placement of devices and diagnostics. The device 100 can also be in the form of interventional devices for use in procedures on the vasculature. Such catheters, sheaths, and devices are well known, and, thus, the general features of the device 100 for these embodiments can be in accordance with conventional devices. The device 100 could further include one or more transducers 210, along with the other components required to provide ultrasound imaging using the transducers 210 as discussed herein.

The device 100 can further be adapted for use in procedures on the nasal passages, sinuses, and pharynx and for accessing the nasal passages, sinuses, and pharynx. In these embodiments, the device 100 can be in the form of a catheter or sheath that provides access to a desired site of the nasal passages, sinuses, and pharynx, thus allowing therapy delivery, intervention, placement of devices and diagnostics. The device 100 can also be in the form of interventional devices for use in procedures on the nasal passages, sinuses, and pharynx (e.g., devices for therapy delivery, intervention, placement of devices and diagnostics). Such catheters, sheaths, and devices are well known, and, thus, the general features of the device 100 for these embodiments can be in accordance with conventional devices. The device 100 would further include one or more transducers 210, along with the other components required to provide ultrasound imaging using the transducers 210 as discussed herein.

The device 100 can further be in the form of devices used to treat and address chronic problems and, as such, can be delivered and lodged in body cavities, organs, or other anatomic locations for long term monitoring or anatomy or function or dynamics including hemodynamics. In these examples, the device can be in the form of a catheter or sheath or other conventional chronic treatment or monitoring device that can be lodged at a desired site. The device 100 would further include one or more transducers 210, along with the other components required to provide ultrasound imaging using the transducers 210 as discussed herein.

In some embodiments, the present device 100 can further be integrated with other non-ultrasound imaging modalities including infrared, laser, optical coherence, fiber optic instruments including, but not limited to endoscopic mapping. For example, the body member 200 can further be provided with a fiber optic lumen through which an optical fiber is insertable.

The present device 100 can be used to provide a three-dimensional mapping system solely using the incorporated ultrasound system or in connection with other imaging modalities such as computed tomography, magnetic resonance, videoscopy. When the device is in the form of a catheter or sheath, this will allow stereotactic and remote/robotic operation of devices inserted and manipulated through the device 100. In such a system, an imaging modality (ultrasound, CT or MRI) can be used to generate a 3 dimensional image. The device will interactively use the generated images to be directed either manually or through an automated or semi-automated process for deployment to a target area displayed in the 3 dimensional image. The device 100 is generally used in connection with an ultrasound display system (B mode image or 3D image) that interfaces with the device to produce and display the images.

The devices 100 can be used to perform any variety of medical procedures including those set forth herein. The general features of these procedures is in accordance with conventional procedures and further make use of the integrated imaging system to provide visualization while accessing and performing procedures at the target site.

In one embodiment, the device 100 can be used to provide pericardial access and effusion. In general, imaging procedures, such as transthoracic imaging, can be used to confirm the location of desired effusion. The surgeon can then mark an optimal entry site on skin. The skin and subcutaneous tissue can be infiltrated with lidocaine or other agent, followed by a small stab incision on the skin. The device 100 can be inserted and advanced to the site. The device can be attached to a syringe (e.g., a 1-cc, 5-cc, 10-cc, 20-cc, 30-cc, 40-cc, 50-cc or larger syringe) before or after insertion and advancement. The device 100 can be used to provide ultrasound images as the device 100 is advanced to the pericardial lining. Using the images provided by the device, the pericardial lining can be punctured using the needle 208, and the surgeon can confirm backflow in the device/syringe. The elongate body 200 can be advanced, and the needle 208 removed. A guide wire can then be advanced to the site via a lumen 206. The body member 200 can be removed and a sheath advanced over guide wire. Pericardial fluid can then be drained to dry. Transthoracic ultrasound or ultrasound using the present device 100 can then be used to confirm proper drainage. In this regard, as discussed above, devices of the invention can be especially useful in loculated or compartmentalized effusions in the heart (pericardial), abdomen (ascites), chest, or abscesses in any organ or body cavity. The distal end imaging (particularly in real-time) can allow safe and accurate access to multiple compartments and ensure safe and complete drainage.

In another aspect, as discussed above, a device of the invention can be utilized to obtain biopsy or material (including) fluids for testing from various organs or fluid collection sites through such pericardial access, or other entry into a patient. Now, pericardial access procedures and methods will be described in some detail with reference to FIGS. 6A-6L and the inflation and deflation of balloons for sealing a pericardial lining will de discussed with reference to FIGS. 7A-8C.

Pericardial Access

With reference to the embodiments described by FIGS. 1-5, the device 100 can be used, for example, to provide pericardial access without effusion, for example, as shown in the exemplary procedure illustrated in FIGS. 6A-6L. In general, imaging procedures, such as transthoracic imaging, can be used to confirm the location of the heart. The surgeon then can mark an optimal entry site on a patient's skin surface (for example, site 730 of FIG. 6E) considering optimal approach angles per FIG. 6A. Site 730 is shown but other sites may be selected depending on the desired approach angles of FIG. 6A. The skin and subcutaneous tissue can be infiltrated with lidocaine, followed by a small stab incision on the skin. The device 100 (FIGS. 1-5) can be inserted and advanced to the site from the surface site among various approach angles as per FIG. 6A. The device can be attached to a syringe (e.g., a 20 cc syringe loaded with saline and lidocaine or other agents) before or after insertion and advancement of the device 100 into the pericardium. The transducer 210 can be used to provide ultrasound images as the device 100 is advanced to the pericardial lining 700 (FIGS. 6A, 6G-L and 7) or camera imaging may be used to some advantage via a fiber optic lumen and distal lens. Using the images provided by transducer 210 in combination with external ultrasound transducer assemblies such as 710, 730 of FIG. 6E, the pericardial lining 700 and site of interest can be located, for example, per FIG. 6G and then punctured using the needle 208 per FIG. 6H.

Now a remote wireless transducer will be briefly explained with reference to FIGS. 6B-6E. Referring to FIG. 6B, there are shown a top view FIG. 6B-1 and side view FIG. 6B-2 of a first plurality of embodiments and aspects of a multi-plane transducer unit comprising a rotatable linear array of transducer elements including a housing. The housing may be mounted by securing material to a body of, for example, a patient or victim. The transducer array or element may be remotely controllably rotated and otherwise remotely controlled by wired or wireless signals transmitted toward the array from a remote work station. An operator need not be proximate the patient's body to manipulate or control the transducer elements or housing. Transducer 101 may comprise a single transducer element for ultrasonic transmission and reception of reflected sound waves or a linear array 102 of transducer elements mounted, for example, in a circular manner from a top perspective as a diameter of the circle or at the center of the circle comprising housing 103. An arrow indicates an angle of rotation in a counter-clockwise direction of the transducer element or a linear array 102 within housing 103. Typically, an angle of rotation of 180 degrees when used with a linear array 102 will permit the collection of a plurality of image planes, for example, of the heart over which the array within housing 103 may be located and fixed to the body surface, in this case, a cylindrical housing as seen from top and side views forming a circular footprint on the body surface. The housing 103 is fixed to the surface of a human body, for example, in a position at the center of the chest or other position depending on desired approach angle per FIG. 6A to monitor the heart and approaching sheath/catheter apparatus 100, 200 of FIGS. 1-5. The top surface of the side view more clearly shows transducer 101 which may rotate within the housing 103. The top surface of housing 103 intended to be fixed to a patient contains an impedance matching substance which may be complimentary to the application of a suitable impedance matching gel. Fastening or securing material 105 is shown in top and side views for fixing the housing to a human body skin surface with the transducer/impedance matching surface facing the human body surface. Within the housing 103 is also contained at least one motor, in the side view embodiment of FIG. 6B-2, a motor 108 for rotating a transducer element or linear array 101, 102. Also located within the housing 103, for example, in the vicinity of the motor may be a wireless transceiver and antenna (not shown; see, for example, FIG. 6C, motors 216, 218, 220, 222) and other circuitry as necessary for receiving motor control signals and other known ultrasound control signals such as on/off, mode, depth, focus and the like. Also, not shown is a battery or power system for powering the motors and circuits requiring power. Alternatively to a wireless device, housing 103 may have a control cable or wire 104 for transducer output, power, motor control and the like.

Cable 104 may lead to a work station console, preferably remote from a patient bedside and operate in a similar manner to known cables used with devices such as a Toshiba PowerVision™ ultrasound machine, the difference being that the depicted cable further includes a rotation motor control lead or leads or a data line of such cable which further incorporates motor control data in a serial data stream. Cable 104 may include motor wiring 106 to rotation motor 108 for control and power purposes. Cable 104 may further comprise transducer wiring 107 for power, control and image collection purposes.

As will be described herein with reference to FIG. 6C, further motors 108 may be provided for twisting linear array 102 (motor 222) to permit a different direction of sound wave emission and/or reception, and for providing two directions, for example, lengthwise and widthwise (x and y) axis movement in the plane of the human body surface (motors 218, 220) and according to how a, for example, rectangularly shaped housing 103 is placed on the body, i.e. an x and y axis are considered in relation to the housing. The housing 103 may be mounted at an angle (see, for example, manner of fixation, adhesive, per FIG. 6E to the human body). Motor 108 may comprise an optional gear assembly 109 (FIG. 6B-2 for more accurate, for example, incremental movement of array 101, 102. Motor 108 is preferably a micro or miniature linear motor known in the art for turning a rotor and optional gear assembly for rotating the coupled transducer element or linear array 101, 102 at incremental steps such as one degree steps from a vertical or horizontal orientation (vertical shown) through 180 degrees—clockwise or counterclockwise. In this manner, a linear array 101, 102 may capture 180 different planes of view of, for example, a heart under observation, and a three dimensional view may be constructed using known software data analysis processes. Of course, the three dimensional analysis is improved and made stereoscopic if pairs (or more than two arrays) of devices at different observation locations according to FIG. 6B are used as will be described in conjunction with a discussion of FIG. 6E. A transceiver (not shown) or a cable 104 may report the actual position of the linear array to a remote work station (FIG. 6F) as a value, for example, between 0 and 180 degrees.

Typical sizes for a cylindrical transducer housing 103 as shown in FIG. 6A may be from 1 cm in diameter to 3 cm in diameter. The height of the cylindrical housing may be similar or less than 1.5 cm.

Figure 6D:
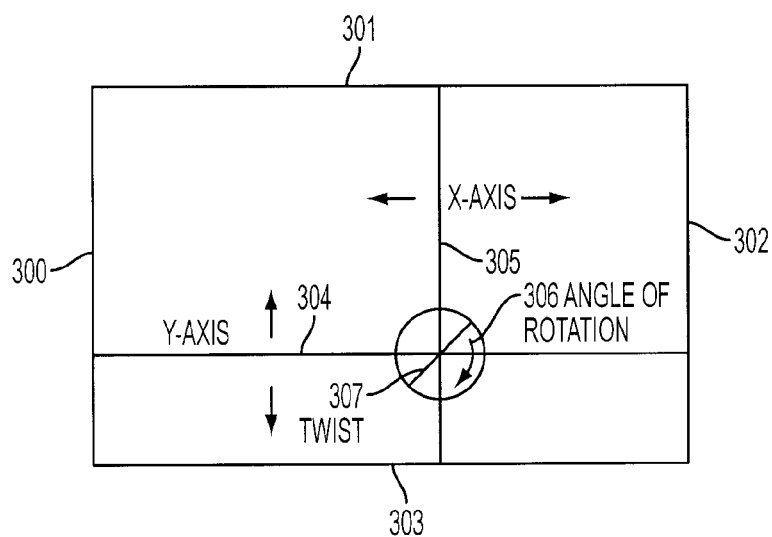
Figure 6E:
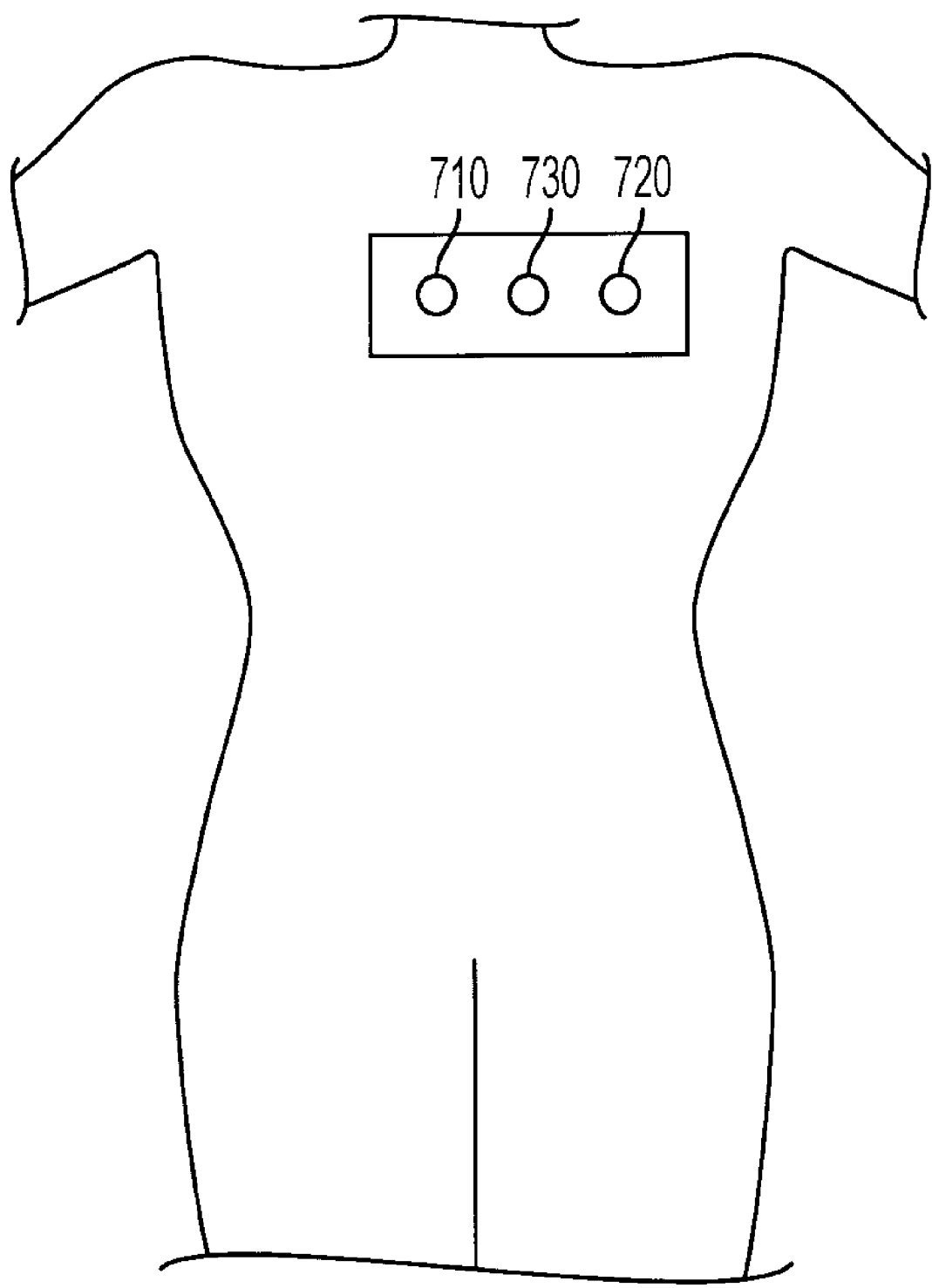

Referring briefly to FIG. 6D, the surface proximate to the body of a housing 103 may comprise a rectangular shape and linear motors may move small rods carrying, for example, a transducer array to a particular x, y coordinate ranging from 0 to 10 cm in one direction to 0 to 12 cm in the other direction within its footprint on the body surface in incremental steps, for example, of 5-20 mm. In a further embodiment as described above, a motor 222 may be provided and mounted to twist a linear array as well as provide an incremental angle of rotation, again, within a range of 0 to 180 degrees with a default position at 90 degrees, or directly pointing sound waves into the human body.

FIG. 6C provides a schematic block diagram for embodiments and aspects of a wireless device as shown in FIG. 6B including a transceiver (which may be a wireless telecommunications transceiver), a transducer control unit, a battery, at least one motor for rotating a linear transducer element array, the linear transducer element array and analog to digital circuitry for converting collected image data to digital form for transmission via the transceiver. In FIG. 6C, a wireless embodiment of a remotely manipulatable ultrasound transducer is assumed. Battery supply unit 222 is preferably a rechargeable lithium battery known in the art that powers all units requiring power within a housing 103.

Figure 6F:
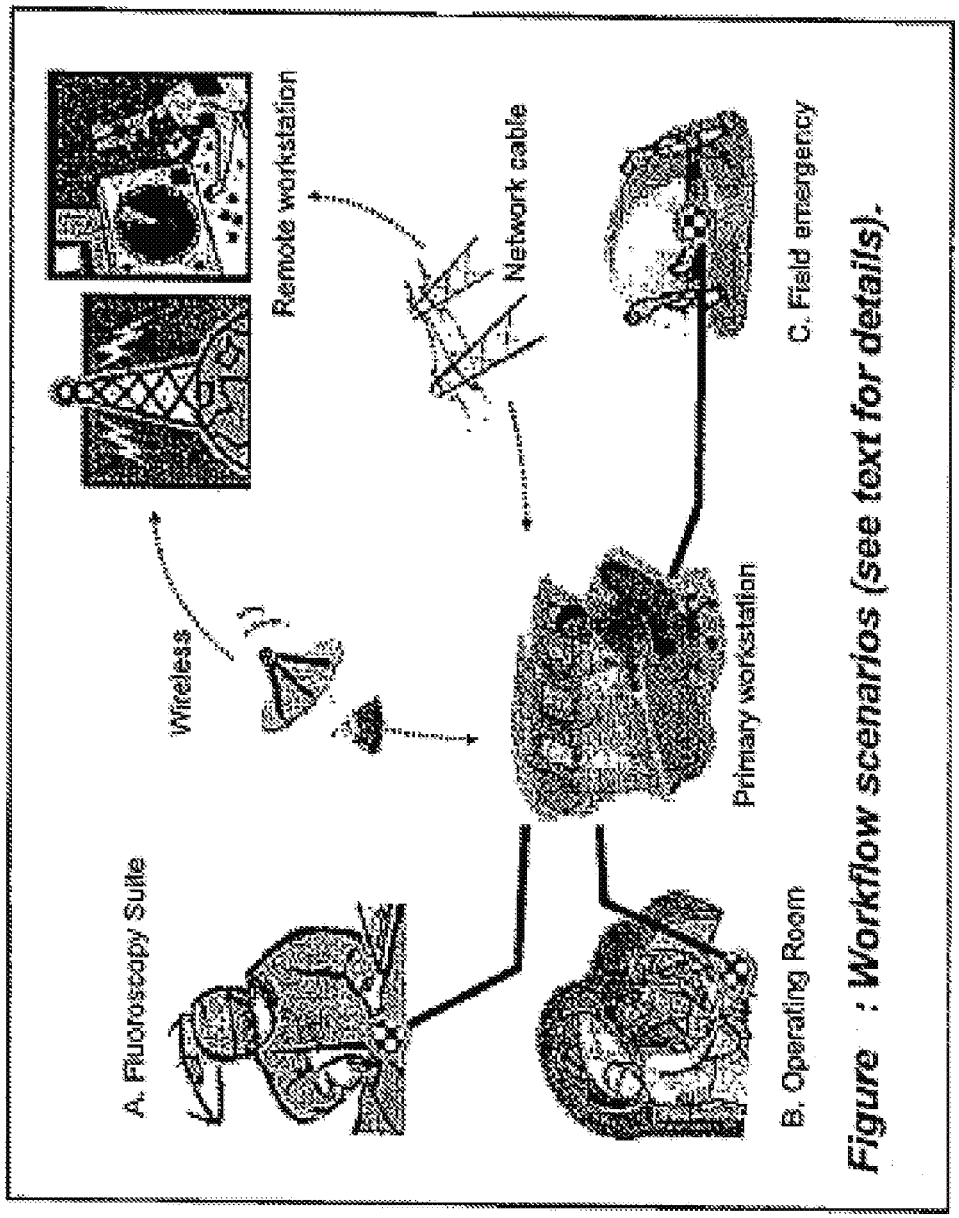

Transceiver 205 is an alternative to a control cable 104 for transmitting and receiving information and may receive and transmit a digital data signal via radio frequency antenna 201. While these figures depict what may be construed as a serial data stream, the depicted data may be sent in parallel or serial format and in any order. Known telecommunications protocols may be utilized if the transceiver transmits and receives by radio frequency signal such as WiFi, blue tooth, Wimax and the like for a wireless local area network. As is known in the art, infrared and ultrasound may be used as well as other light frequencies than infrared as a through-the-air transmission media to the work station (FIG. 6F). On the other hand, light waves are typically incapable of penetrating through walls and require a line of site transmission path. Yet, by way of example, light wave transmission is feasible; for example, a light wave transceiver connected to a work station may be mounted, for example, in the ceiling of a surgical operating arena and a unit mounted to a patient facing upward may communicate with the ceiling mounted unit in a line of site. As described above, since a cable 104 provides a direct link to a remote work station, cable 104 need not necessarily transmit data uniquely indicative of a given transmitter, transducer or work station because the cable 104 may comprise a direct link between known devices. If any other device is connected to cable 104, then addressing using a unique address (or telephone number) or other identifier should be used for a connected device. Transceiver 205 may receive a data signal from a work station, demodulate the signal and output a demodulated baseband data signal including data to controller 210 which may be a microprocessor, application specific integrated circuit or other control circuit which may be designed and fabricated in a manner well known in the art. In the other direction of transmission, the transceiver 205 may receive image data for one or more planes or sequential images and other signal including actual position data from controller 210 for transmission to a uniquely identified remote work station (FIG. 6F).

Following the path of a received signal at antenna 201, the received signal may be received at radio frequency at transceiver 205, demodulated and an Rx data output signal passed to controller 210 for processing. Controller 210 authenticates the signal as directed to it by means of the transmitted unique transducer identification code. In addition, the signal may require processing in accordance with well known protocols for decompression, decryption, parity and other data error detection and correction algorithms and the like (not shown). In one embodiment, for example, for multi-planar imaging purposes, the transducer array 225 is linear and may be rotated. A rotate signal which may indicate an angle between 0 and 180 degrees in incremental steps of, for example, one to five degrees can indicate rotation in a clockwise or counterclockwise direction or indicate an angle to which the transducer array or element is to be rotated (for example, from 90 degrees, actual present position, to 120 degrees, desired position) is received and passed to linear motor 216 having a rotor for rotation using, possibly, an optional gear assembly 109 for turning the linear array 102 to a desired angle of rotation.

In an alternative embodiment, for example, for therapeutic purposes, still as shown in FIG. 6C, a direction of sound wave propagation, depth and the like signal are received and reported to actuate twist motor 222 to a desired angle of twist in addition to a desired angle of rotation via motor 216 to, for example, deliver a therapeutic sound wave to a given body organ or sub-tissue layer at a given transmitted depth, for example, represented by a sound wave power level, within the patient's body from the transducer 102, 225. In an embodiment paired with another unit (units 710, 720 of FIG. 6E), the angle of twist and rotation may be synchronized so that one transducer array 102 may cooperate with another transducer array as sound wave transmitter and sound wave receiver for together providing image data either individually or together.

In a further alternative embodiment, the transducer array 102 or transducer element may be manipulated in two directions, perpendicular to one another, along the patient's body surface, denoted an x direction and a perpendicular y direction or axis as shown in FIG. 6D. The transceiver 205 outputs such control data to controller 210 which then actuates motors 218 for x axis movement and 220 for y axis movement of transducer element or transducer array 102 (FIG. 6B), 225 (FIG. 6C). Also shown in FIG. 6C are x, y axis 227, 229 which are controlled by motors 218, 220. When arriving at the x, y position of interest, the transducer 102, 225 may be rotated or twisted or rotation and/or twisting/rotation may occur en route to the x, y position of interest. Feedback to the remote work station (FIG. 6F) may be provided via actual data indicating all parameter values of interest, on/off, focus level, depth, x axis, y axis, angle of rotation and angle of twist.

Also, controller 210 may be in receipt of off/on, focus control, mode, depth and other control data which is passed to transducer 102, 225 for proper operation, for example, to regulate the amount of power delivered to transducers for sound wave emission or for focusing the array. This control lead or collection of leads is shown as data line 235.

The output of transducer array 102, 225 may be raw image (reflected sound wave) data similar to that obtained by a hand-held transducer array known in the art. It may be in analog form and provided to an A/D converter 214 (FIG. 6C) for sampling at an appropriate sampling level. The data signal output of A/D converter 214 may be further compressed at data compressor 212 prior to formatting at controller 210 for transmission at transceiver 205 and/or storage at memory 207. These circuits 214 and 212 are shown as separate circuits but may, together with controller 210 be in the form of a single application specific integrated circuit (ASIC) or provided as separate circuits. Memory 207 may be on board a microprocessor chip or provided separately. In one embodiment, memory 207 may comprise a removable memory for uploading data to a device for telecommunications transmission. The image and other data prior to transmission or for long term storage may be temporarily or more permanently stored in memory 207. Similarly, memory 207 may be utilized for temporarily storing control data as received from transceiver 205 and prior to being operated on by controller 210. In one embodiment as will be described herein, there is no data transmission via cable or wireless means.

FIG. 6D, in association with FIG. 6B, provides an overview of a mechanical arrangement to be contained within a housing 103 of rectangular or square embodiments of a transducer unit for manipulating a transducer or linear transducer array in two directions, for example, along an x axis and a y axis and to provide an angle of rotation and a twist angle at a desired x, y coordinate pair to redirect a sound wave emitted by a transducer or linear array of transducer elements whereby it is envisioned that a footprint on a patient body surface is rectangular or square and relates to the embodiments and circuits of FIGS. 6A and 6B. Assume the rectangle housing comprises guide wires or rods 300, 301, 302 and 303 on which are provided y-axis rod 304 which may be moved in an up and down direction shown via a corresponding motor 220 and gear assembly not shown to incremental steps along the y axis. Similarly, there is provided x-axis rod 305 which may be moved to the left or the right direction shown via corresponding motor 218 and a gear assembly not shown. X-axis rod 305 and Y-axis rod 304 intersect at a desired point where an array or element may be affixed via further motors 216, 222. For example, rotor 306 of motor 216 (in combination with an optional gear assembly 109) provides rotation of a mounted transducer array 102, 225 or transducer element to a predetermined or desired angle of rotation. Motor 222 provides twist 307 to linear array or element 102 to change direction of sound wave transmission or reception with 90 degrees—straight down—being a default position for twist.

FIG. 6F shows a workflow scenario whereby the primary workstation for processing and displaying ultrasound images is remote from a fluoroscopy, operating room and the like and, if necessary, shielded from adverse impacts of radiation such as magnetic resonance. One further limitation of using ultrasound in an operating suite is electrocautery procedures which may degrade collected image signal quality when the electrocautery apparatus is in use. Referring to FIG. 6F, there may be situations where the ultrasound operator be optimally protected, for example, in a fluoroscopy suite where the operator is exposed to radiation and would otherwise need a heavy lead suit. Even with the lead suit, the operator would typically have to move a 400 or 500 pound ultrasound machine back and forth from along side the operating table to away from the table when a C arm is being used. Now, the ultrasound operator may sit at a remote work station after placing the remotely manipulatable transducer or transducer array (FIG. 6C) on the surgical patient and then sit behind a lead shield to manipulate and operate the transducer or linear transducer array remotely at their primary work station. Also, there is typically inadequate space in an operating room for an ultrasound operator, for example, next to a surgical operating table. The operator may place the transducer and then remotely manipulate and control and view images from the remotely manipulatable transducer at the work station. Their work station can be located in a corner of the operating room or outside the operating room and the operator communicate by telecommunications means with the surgeon (or other operating room personnel).

Figure 6G:
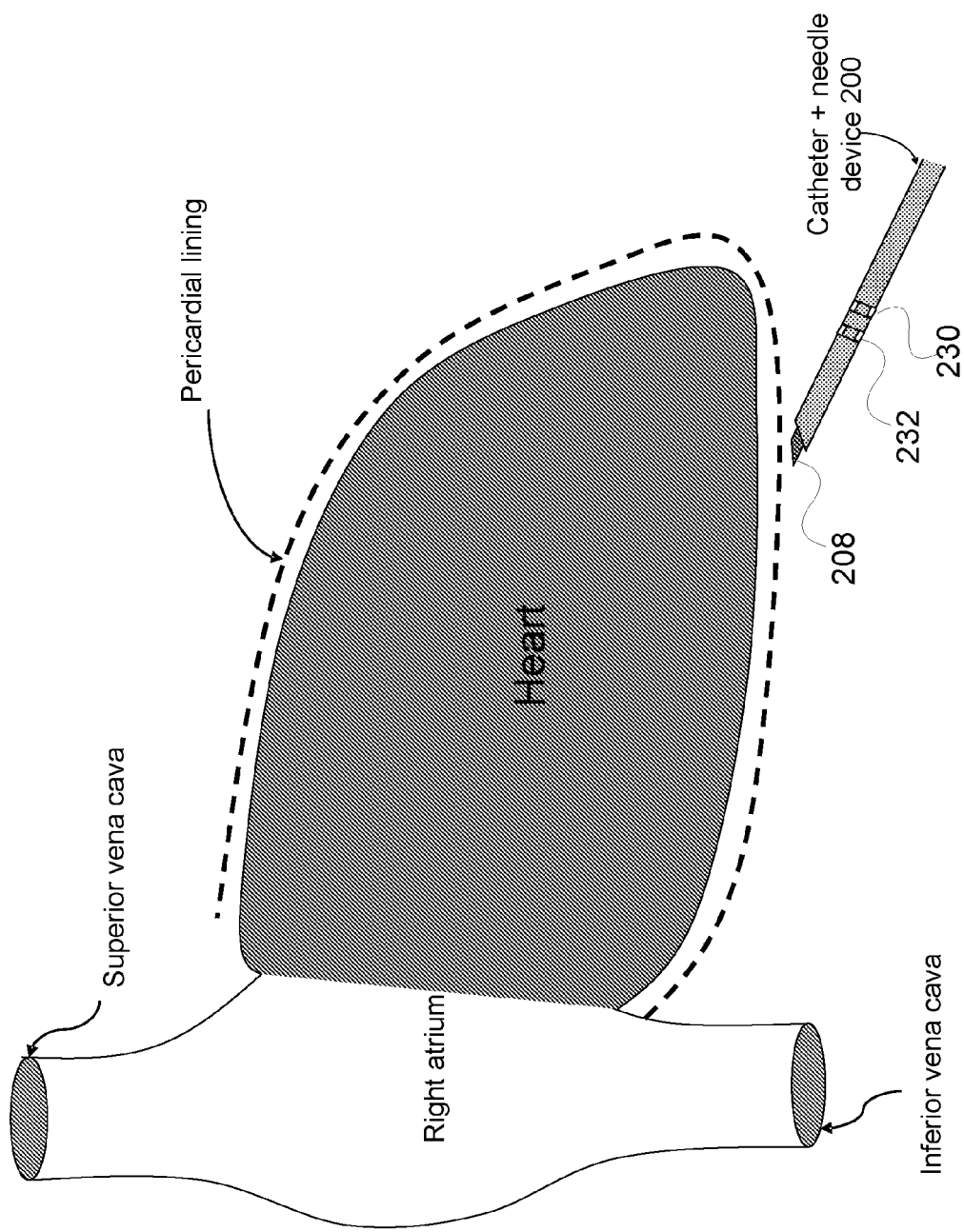
Figure 6H:
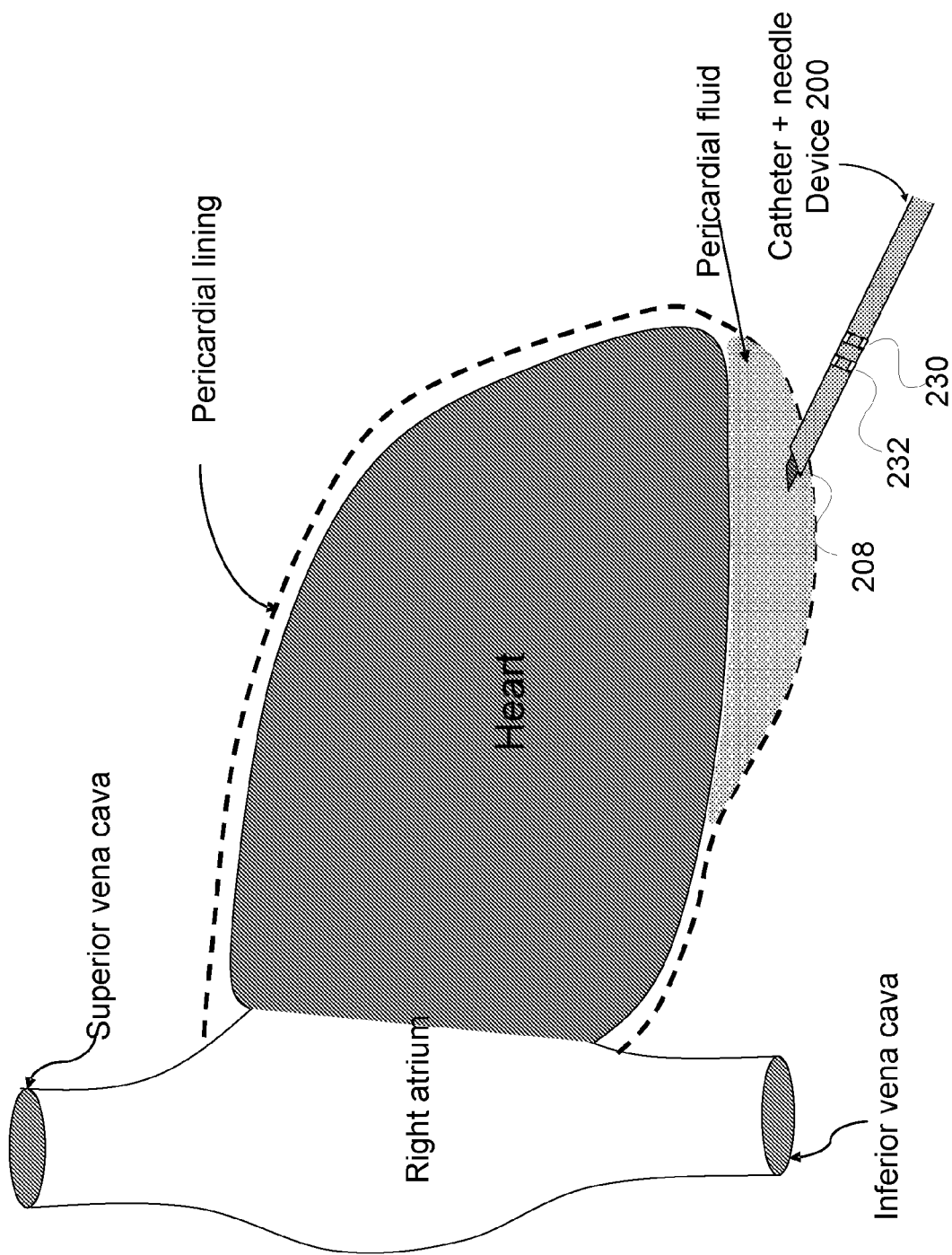
Figure 6I:
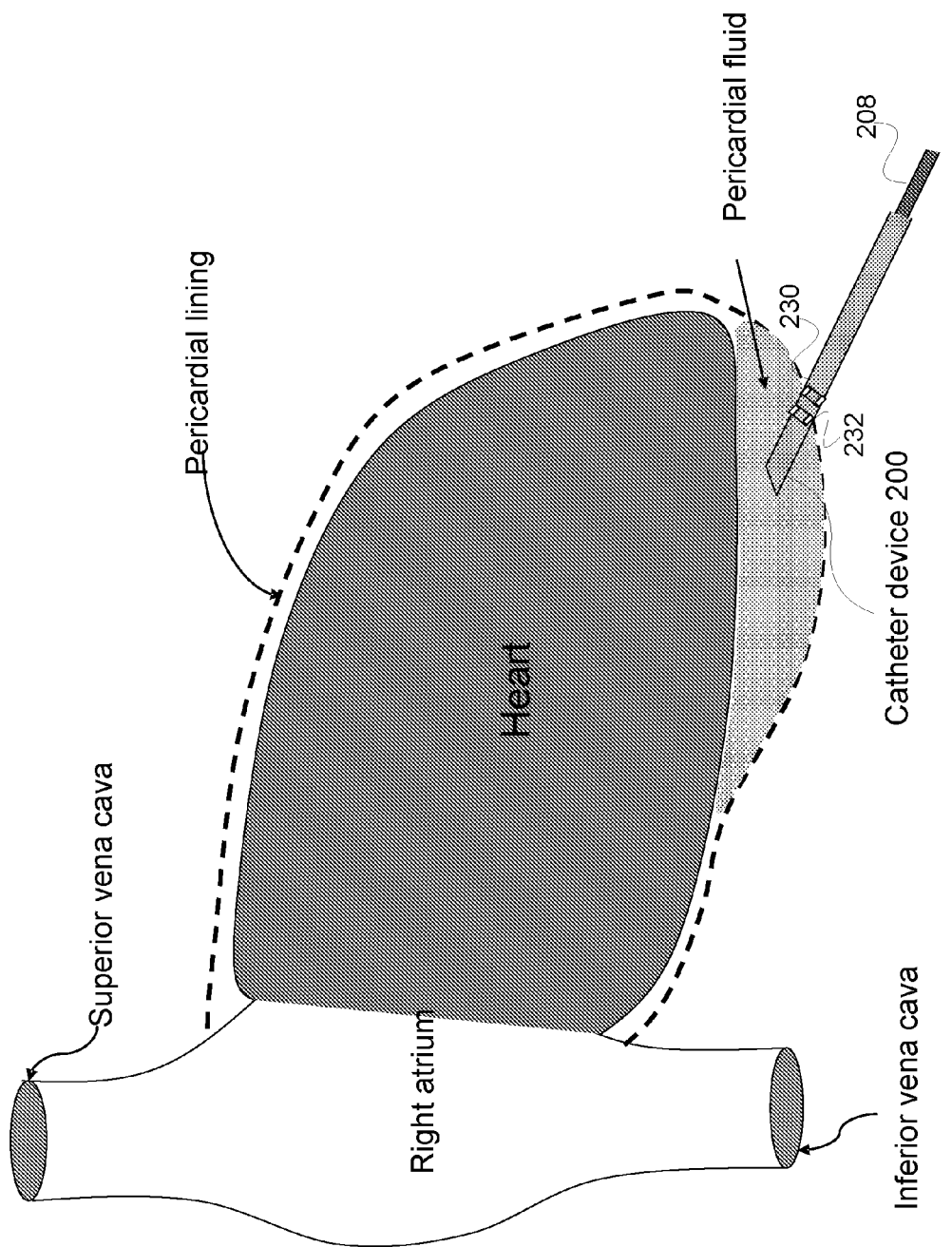
Figure 6J:
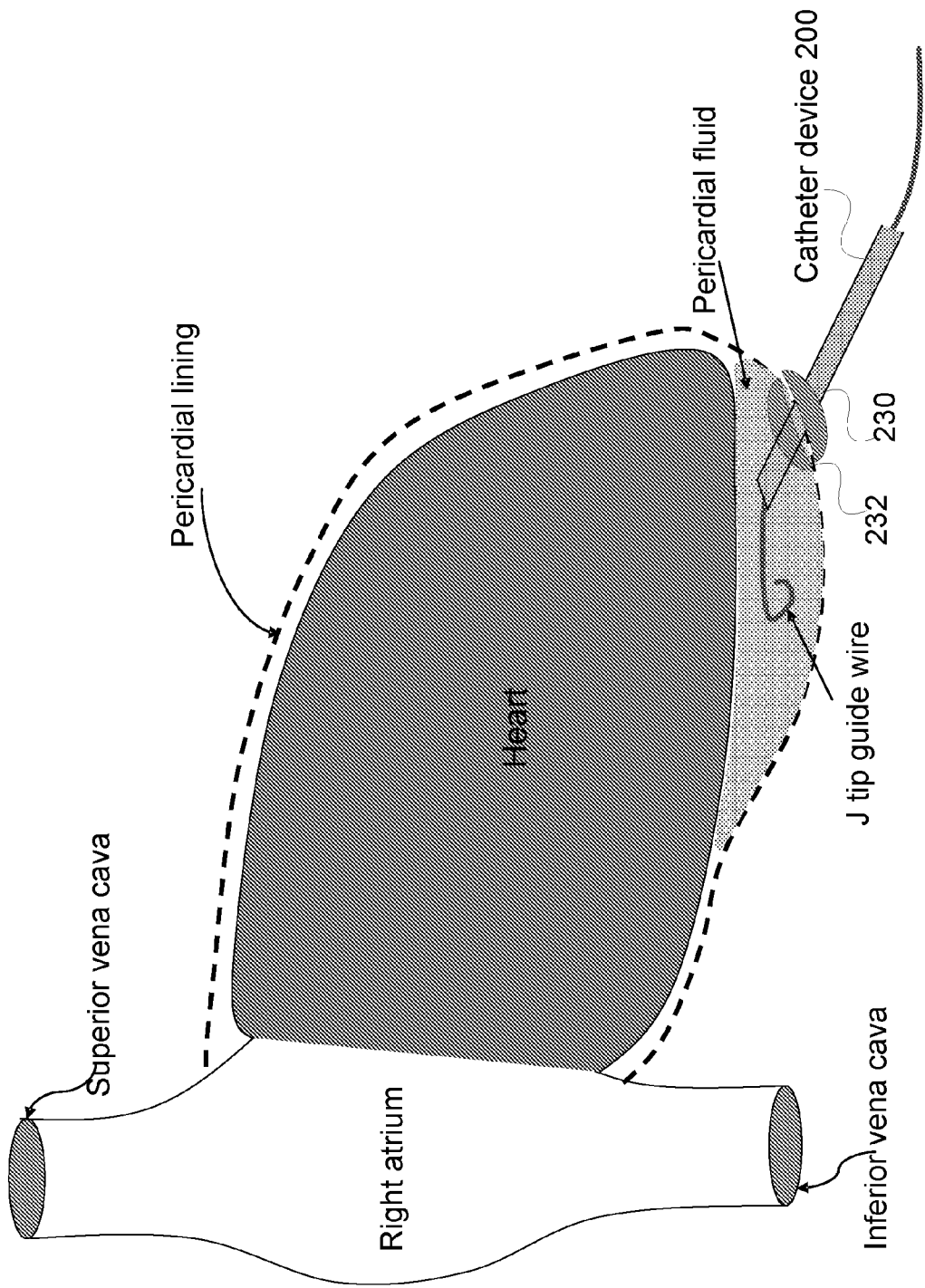
Figure 6K:
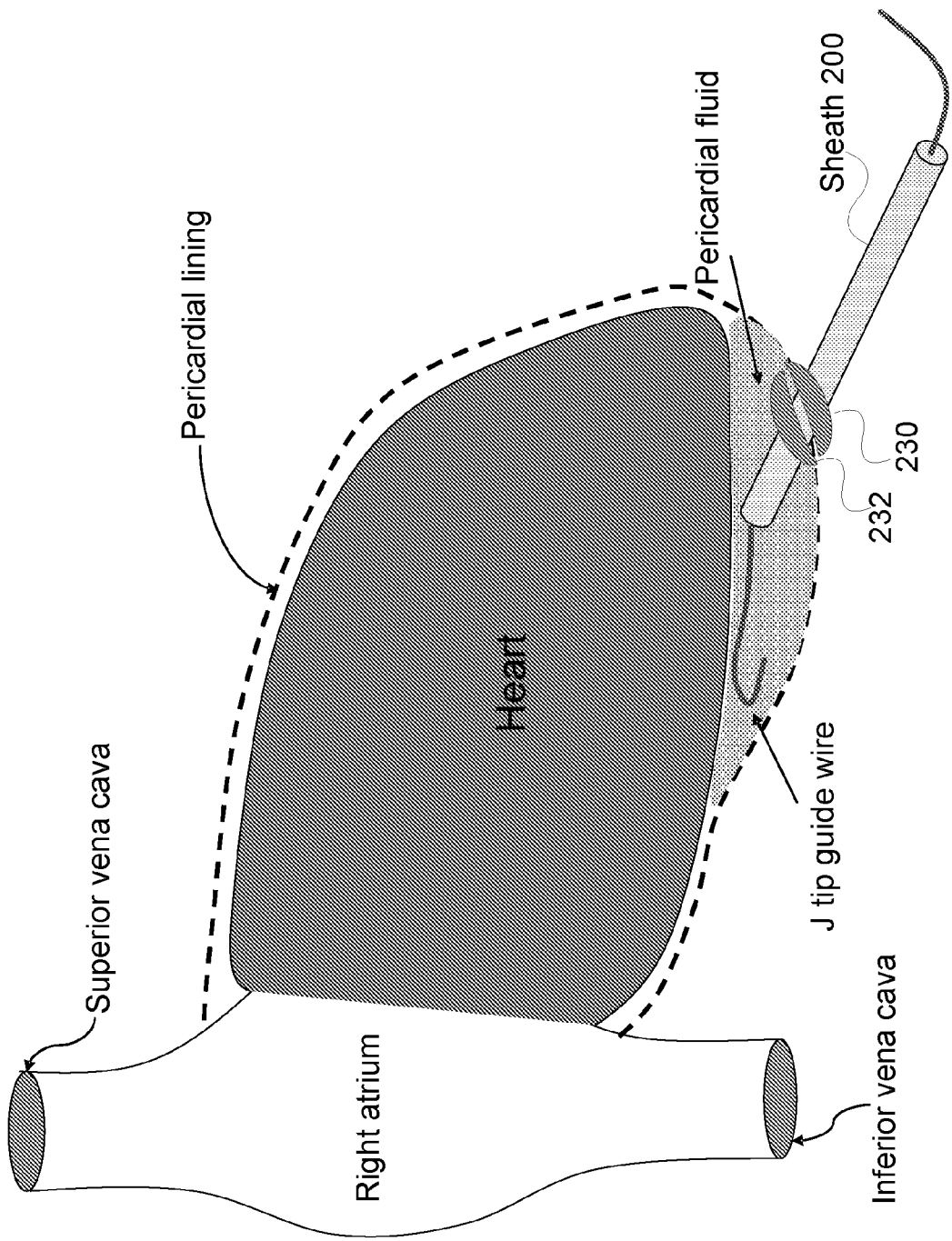

Referring to FIG. 6G, a catheter and needle are shown proximate the pericardial lining at a desired approach angle. Syringe contents can be injected through the needle into the pericardium after the needle has pierced the pericardial lining. The position of the fluid can then be confirmed using the device's ultrasound system or external ultrasound system, and the elongate body 200 can be pushed further, under guidance, into the pericardial space. Additional material from the syringe can be injected, if necessary, to create a safe "pericardial pocket". Referring to FIG. 6I, the needle 208 can be removed. Referring to FIG. 6J, a pericardial lining may be located and a distal balloon 232 inflated followed by a proximal balloon 230 after the body 200 is pulled so that the distal balloon makes sealing contact with the pericardial lining 700. In an embodiment involving a balloon assembly per FIG. 2F, the pulling of the catheter/sheath moves the slidably moveable assembly 300 so that the channel 236 engages indentation 310 and balloon material 301 is inflated. Then, the catheter/sheath is pushed so that the assembly slides to a position where channel 236 is in position to inflate balloon material 302. Then, a guide wire, for example, a J tip guide wire may be advanced via the device 100 per FIG. 6J.

Figure 6L:
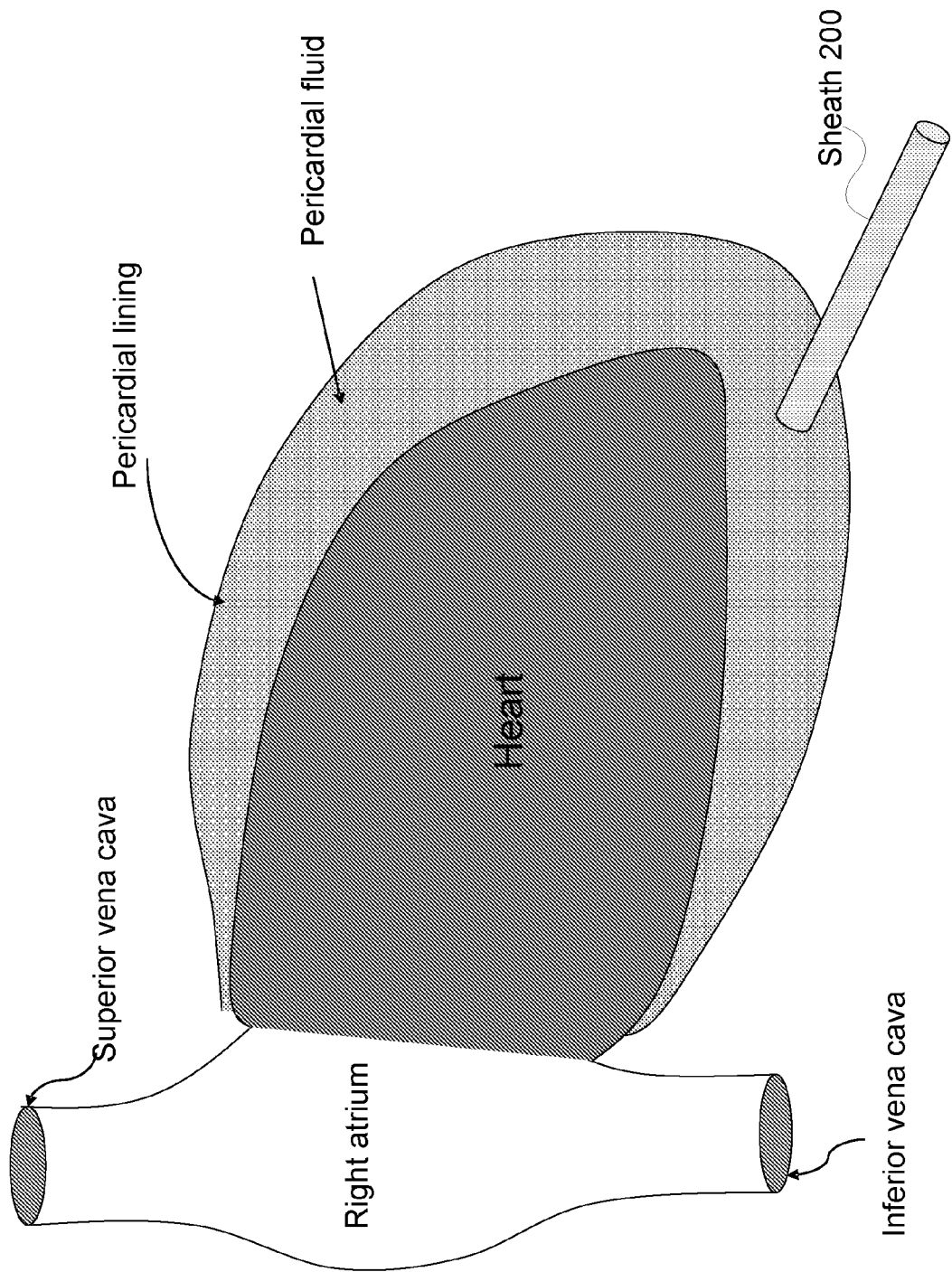

With the guide wire properly placed, the imaging catheter may be withdrawn and replaced with a sheath. To do so, the balloons 230, 232 are deflated, and the imaging catheter removed. Once the imaging catheter device 100 is removed, a sheath may be advanced over the guide wire per FIG. 6K. In a similar manner as the imaging catheter, dual balloons 230, 232 may be provided on such as sheath to lock and seal the sheath to the pericardial lining. Saline (up to 100-150) can then be injected into the pericardium and the pericardium can be monitored with transthoracic ultrasound or ultrasound using wireless devices or the sheath may comprise a distal ultrasonic element or array. Interventional and/or diagnostic devices can then be advanced through the sheath of FIG. 6K. FIG. 6L shows the sheath being removed with any provided balloons deflated. In summary, for example, the planned procedure of FIG. 6A-6L may be performed, for example, and pericardial fluid aspirated as necessary. The sheath can then be removed and the incision at the body surface closed with, for example, TEGADERM® dressing or STERISTRIPS®. The pericardial lining may self heal or be sutured if necessary.

Such access to the pericardial space thus can permit a variety of discussed procedures including e.g., epicardial mapping, lead placement, intracardiac interventions, and the like. Access to other organs, structures, and spaces can be performed in similar fashion with appropriate procedural modifications specific for the particular organs, structures or spaces.

FIGS. 7A-7C show particular details of inflation of balloons 710, 720. FIG. 7A shows a sheath or catheter having distal balloon 710 and proximal balloon 710 deflated at the time the sheath/catheter has pierced the pericardial lining 700. As suggested above, the channels to the balloons may be distinguished by contrast agent and thus viewable from surface ultrasound transducers or device side-mounted transducers as shown in FIG. 4A may assist locating the organ wall (in this case, pericardial lining). In particular, FIG. 7B has been enhanced to show transducers 224a, 224b and 224c for locating the pericardial lining 700. FIG. 7B also shows a partially inflated step where balloon A, 720, the distal balloon has been filled with inflation fluid by a corresponding inflation channel and is pulled so that it lies against the pericardial lining, thus partially sealing it from leakage. Balloon 710 remains deflated. Then, balloon 710 is inflated via a corresponding inflation channel as shown in FIG. 7C creating a round sandwich of balloons, for example, creating an appearance of automobile tires on each side of pericardial lining 700. The withdrawal of sheath/catheter operates in reverse order— FIG. 7C, FIG. 7B and then FIG. 7A.

Figure 8C:
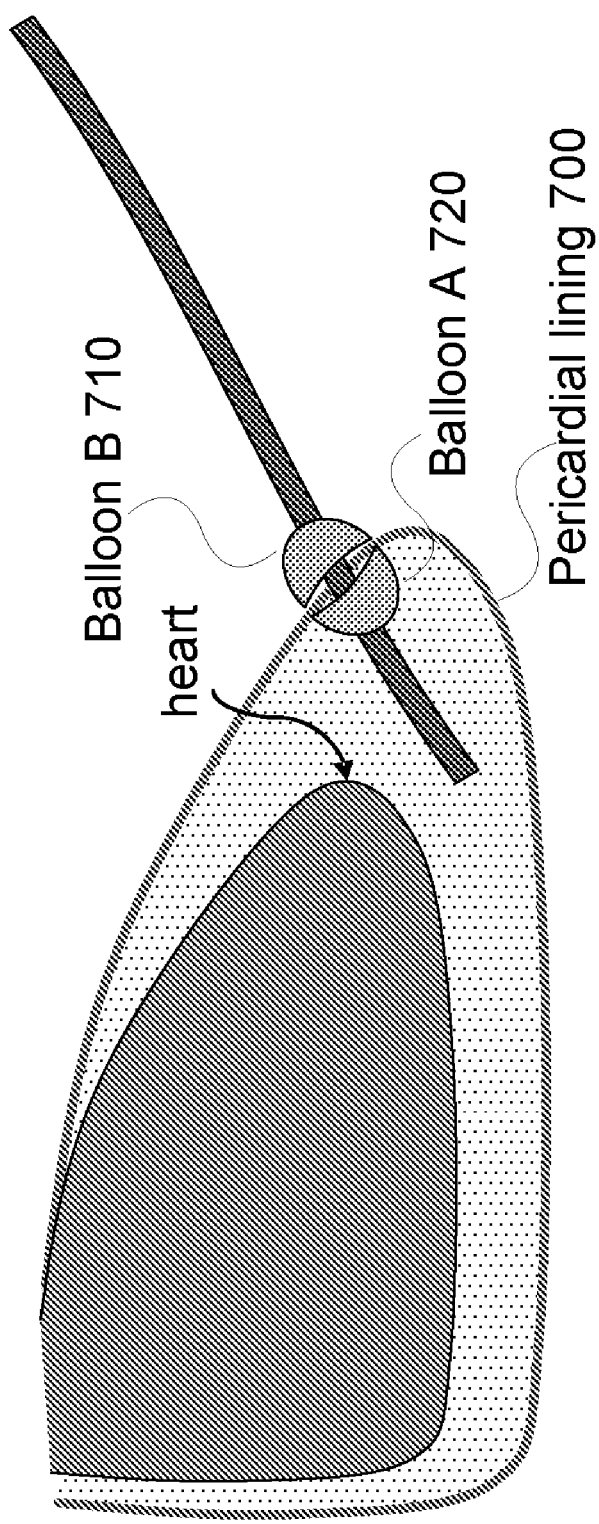
FIGS. 8A-B show the sandwich balloons in a deflated and an inflated state as deployed on the exterior of a sheath or catheter having inflation channels provided therein from a proximate end to each balloon.

FIGS. 8A and 8B provide similar views to FIGS. 7A-7C where FIG. 8A shows a deflated state of balloons 710, 720 and FIG. 8B shows an inflated state. Referring to FIG. 8B, an anchoring portion that is slidably moveable may be moved to contact the skin surface. In combination, the slidably moveable anchor 218 helps lock the catheter or sheath in place with the sandwich balloons 720, 710 sealing and locking to the pericardial lining 700. FIG. 8C shows deployed and inflated balloons sandwiching the pericardial lining where the sheath or catheter is extended within the pericardial space.

All documents specifically referred to above are incorporated by reference herein in their entirety. Although the instruments and methods discussed above and primarily illustrated and described herein provide instruments that also can be adapted for performing laparoscopic radical prostatectomy on humans, it will be appreciated by those skilled in the art that such instruments and methods also are adaptable for use in other particularly delicate surgical procedures (both open and laparoscopic) as well as in performing various veterinary surgeries and biopsies. Further, while the instruments and methods are primarily illustrated and described in connection with clamps and dissectors, other instruments (e.g. various laparoscopic and open surgery instruments such as graspers, scissors, forceps, biopsy punch, biopsy spoon, and hooks) could likewise be provided as described herein. Further, while several preferred embodiments have been described using specific terms, such description is for illustrative purposes only, and it is to be understood that changes and variations may be made without departing from the spirit or scope of the following claims.

I claim:

1. A medical device comprising:
    an elongate body having a central lumen along the center of a predetermined length of the elongate body and an exterior surface thereof at predetermined radii from the central lumen;
    an ultrasound imaging transducer proximate to a distal end;
    a first balloon and a second balloon at respective first and second different indentations approximately intermediate said predetermined length of the elongate body, the first and second indentations being radially within said exterior surface of the elongate body, the balloons residing in a deflated state within said respective first and second indentations radially within and round the sides of the elongate body, the first and second indentations having a lesser radius from the central lumen than said exterior surface and the first and second balloons being configured to sandwich one of an internal human body wall and a body organ lining in an inflated state during use of the device, the elongate body of the medical device configured for direct access from an exterior surface by a selected approach angle to the interior of a patient via one of said internal wall or lining during use of the device, the balloons in an inflated state configured to seal and to lock the elongate body of the medical device in place at the internal human wall or lining during use of the device;

said first and second balloons and said respective first and second indentations comprising an assembly which is slidably moveable along the elongate body, the assembly being radially within the predetermined length of the elongate body, said first and second balloons being configured to communicate with a single inflation/deflation channel of the elongate body.

2. A medical device as recited in claim 1 further comprising at least one side-mounted ultrasound imaging element, said at least one side-mounted ultrasound imaging element being located between the first and second balloons.

3. A medical device as recited in claim 1 further comprising at least one side-mounted camera imaging fiber optic lens, said at least one side-mounted camera imaging fiber optic lens being located between the first and second balloons.

4. A medical device as recited in claim 1, the elongate body having proximal and distal ends, the device further comprising a slidably moveable anchoring portion at a proximal end of the device, the anchoring portion configured to securing the medical device at the surface of a human body during use of the device.

5. A medical device as recited in claim 1 comprising at least one inflation/deflation channel for inflating and deflating the first and second balloons, the at least one inflation/deflation channel comprising a substantially hollow outer proximate cavity along the exterior surface of the elongate body of the device extending from a proximal end to a vicinity of one of said first and second balloons of the slidably moveable balloon assembly during operation.

6. A medical device as recited in claim 5 further comprising valve apparatus at the proximal end, the valve apparatus for opening and closing the at least one channel to receipt or discharge of inflation/deflation fluid.

7. A medical device as recited in claim 6, said inflation/deflation fluid comprising a saline solution mixture with ultrasound contrast agent.

8. A medical device as recited in claim 6, said inflation/deflation fluid comprising ultrasound contrast agent.

9. A medical device as recited in claim 1 further comprising a remote wireless transducer apparatus configured to be mounting on the patient's skin during use of the device, the device having first and second motors for remote manipulation of an associated ultrasound transducer of said remote wireless transducer apparatus, the first motor for linear movement and the second motor for one of twist and rotation of said associated ultrasound transducer, the remote wireless transducer apparatus having an imaging direction configured to capture image data of the medical device upon insertion into the patient's interior during use of the device.

10. A medical device as recited in claim 1 wherein said device comprises a catheter and needle, the needle configured to pierce said human wall or lining during use of the device, and an ultrasound transducer configured to provide image-guided piercing of said human wall or lining by said needle during use of the device.

11. A medical device as recited in claim 1 wherein said medical device comprises a sheath configured to deliver a guide wire to a predetermined location during use of the device.

12. An image guided catheter comprising:
an elongate body having a center and an exterior surface and configured for direct access from an exterior surface of a human body to an internal human body wall by a selected approach angle during use of the catheter;
distal ultrasound imaging transducer,
first and second indentations of the elongated body, each indentation surrounding and being radially within the exterior surface of said elongate body, each indentation having a distal wall and a proximate wall, the first and second indentations being proximate to one another along and radially within the exterior surface of said elongate body as measured from the center of the elongate body;
first and second balloon material, the first balloon material being respectively fixed to distal and proximate walls of said first indentation and the second balloon material being respectively fixed to distal and proximate walls of said second indentation;
one inflation/deflation channel running from a proximal end of the elongate body to a vicinity of each of said first and second indentations; and
valve apparatus for said at least one inflation/deflation channel, the valve apparatus for receiving inflation fluid for separately feeding each indentation to cause said first and second balloon material to separately inflate,
the inflated first and second balloon material of each indentation being located proximate to one another and configured to sandwich the internal human body wall during use of the catheter, said first and second balloon material configured, when inflated, to seal and to lock the catheter to an internal human body wall during use of the catheter;
wherein said first and second balloon material and indentations comprise an assembly which is slidably moveable along the elongate body, the assembly being radially within the predetermined length of the elongate body and said first and second balloon material being configured to communicate with a single inflation/deflation channel of the elongate body.

13. An image guided catheter as recited in claim 12 further comprising at least one of a side-mounted ultrasound imaging element or side-mounted fiber optic camera lens, said at least one side-mounted ultrasound imaging element or camera lens being located between the first and second indentations.

14. An image guided catheter as recited in claim 12 further comprising a slidably moveable anchoring portion at a proximate end, the anchoring portion configured to secure the catheter at the surface of a human body during use of the catheter.

15. An image guided catheter as recited in claim 12 comprising first and second inflation/deflation channels, said channels comprising substantially hollow outer proximate cavities along the outer walls of the catheter extending from a proximal end to each of said first and second indentations of the slidably moveable balloon assembly.

16. An image guided catheter as recited in claim 12, said inflation fluid comprising a saline solution mixture with ultrasound contrast agent.

17. An image guided catheter as recited in claim 12, said inflation fluid comprising ultrasound contrast agent.

18. An image guided catheter as recited in claim 17, said inflation fluid filling one inflation/deflation channel along the exterior surface of the elongate body of the catheter extending from a proximal end to each of said first and second indentations of said slidably moveable balloon assembly in sequence, said filled inflation/deflation channel configured to identify the location of the image guide catheter in relation to an internal human body wall during use of the catheter with external ultrasound imaging apparatus.

19. An image guided catheter as recited in claim 18 wherein said external ultrasound imaging apparatus comprises a wireless ultrasound transducer comprising a mobile ultrasound transducer, said wireless ultrasound transducer rendered mobile by a first motor for linear movement and a second motor for one of rotation and twist movement of said mobile ultrasound transducer, said mobile ultrasound transducer configured to image said first and second balloon material inflation from human body surface during use of the device.

20. An image guided catheter as recited in claim 12, said catheter further comprising a needle for insertion in a longitudinal lumen extending from a proximal end to a distal tip of the catheter, the needle configured to pierce the internal human wall during use of the catheter.

21. A sheath configured to introduce a medical devices into a human body directly through the chest cavity to an internal human structure during use of the sheath, the sheath having a hollow center, and further comprising:
   first and second indentations, each indentation of said sheath surrounding said sheath, each indentation having a distal wall and a proximate wall, the first and second indentations being proximate to one another and at a predetermined depth radially within an exterior surface of and along said sheath;
   first and second balloon material being fixed to the distal and proximate walls of each of said first and second indentations;
   one inflation/deflation channel running from a proximal end of the sheath to a position approximately intermediate said first and second indentations; and
   valve apparatus for said one inflation/deflation channel, the valve apparatus for receiving inflation fluid for separately feeding each indentation to cause each of said first and second balloon material to inflate,
   the inflated first and second balloon material of each indentation being located proximate to one another configured to form a sandwich to seal and lock a sheath part to the internal human body wall during use of the sheath;
   wherein said first and second balloon material and indentations comprise an assembly which is slidably moveable along the sheath, the assembly being radially within the predetermined length of the sheath, said first and second balloon material and indentations of the assembly being configured to slidably move to communicate with the one inflation/deflation channel of the sheath.

22. The sheath of claim 21, said at least one channel for receiving inflation fluid comprising ultrasound contrast agent for ultrasonic imaging said sheath from a proximal end to a point between said first and second indentations via external ultrasound imaging apparatus.

23. A medical device comprising:
   an elongate body having an inflation channel and an exterior surface;
   an ultrasound imaging transducer at a distal end;
   first distal and second proximal balloons at a position intermediate a length of the elongate body such that the balloons reside in a deflated state within respective indentations within round sides of the elongate medical device body having the inflation channel, the elongate body of the medical device configured to directly access the interior of a human organ from an exterior surface of a human body to a wall of the organ during use of the device, the first distal and second proximal balloons in an inflated state configured to seal the human organ wall at a point of human wall puncture and configured to lock a part of the medical device in place at the human organ wall during use of the device, said first distal and second proximal balloons and respective indentations comprising an assembly which is slidably moveable along the elongate body and being located within a radial cavity of the smooth external surface of the elongate body and at a predetermined radial depth from the exterior surface, such that in a first position of the slidably moveable assembly, the first distal balloon is located over an inflation channel of the elongate body and, in a second position, the second proximal balloon is located over the inflation channel of the elongate body.

24. A medical device as recited in claim 23 further comprising a slidably moveable anchoring portion at a patient skin surface end of the elongate body, the anchoring portion configured to secure the device at the surface of a human body during use of the device.

\* \* \* \* \*